(12) United States Patent
Sato et al.

(10) Patent No.: US 11,794,448 B2
(45) Date of Patent: Oct. 24, 2023

(54) SENSOR DEVICE, METHOD OF MANUFACTURING SENSOR DEVICE, AND VEHICLE SEAT

(71) Applicant: Alps Alpine Co., Ltd., Tokyo (JP)

(72) Inventors: Tadamitsu Sato, Tokyo (JP); Sascha Kunzmann, Schwabsoien (DE); Unmesh Ghoshdastider, Hamburg (DE); Martin Oehler, Braunschweig (DE)

(73) Assignee: Alps Alpine Co., Ltd., Tokyo (JP)

( * ) Notice: Subject to any disclaimer, the term of this patent is extended or adjusted under 35 U.S.C. 154(b) by 427 days.

(21) Appl. No.: 16/898,017

(22) Filed: Jun. 10, 2020

(65) Prior Publication Data

US 2020/0298530 A1    Sep. 24, 2020

Related U.S. Application Data

(63) Continuation of application No. PCT/JP2018/044077, filed on Nov. 29, 2018.

(30) Foreign Application Priority Data

Dec. 15, 2017  (JP) ................. 2017-241148

(51) Int. Cl.
*B32B 3/02*    (2006.01)
*B32B 3/06*    (2006.01)
(Continued)

(52) U.S. Cl.
CPC ............. *B32B 7/025* (2019.01); *A61B 5/27* (2021.01); *A61B 5/6893* (2013.01); *B32B 3/02* (2013.01); *B32B 3/06* (2013.01); *B32B 5/022* (2013.01); *B32B 5/073* (2021.05); *B32B 5/26* (2013.01); *B32B 5/265* (2021.05); *B32B 5/266* (2021.05); *B32B 7/05* (2019.01); *B32B 37/0076* (2013.01); *B60N 2/002* (2013.01); *A61B 5/11* (2013.01);
(Continued)

(58) Field of Classification Search
None
See application file for complete search history.

(56) References Cited

U.S. PATENT DOCUMENTS 6,329,914 B1 * 12/2001 Shieh ............... G08B 13/26
                                                340/561
6,559,555 B1 *  5/2003 Saitou ............. B60N 2/002
                                                307/121
(Continued)

FOREIGN PATENT DOCUMENTS

CN      207912474 U  *  9/2018
DE       19826391 A1 * 12/1999 ............ B60N 2/002
(Continued)

OTHER PUBLICATIONS

Machine Translation of DE-102006027213-A1, Dec. 2007 (Year: 2007).*

(Continued)

*Primary Examiner* — Jeffrey A Vonch
(74) *Attorney, Agent, or Firm* — Beyer Law Group LLP

(57) ABSTRACT

A sensor device has an insulative non-woven fabric and a conductive fabric forming an electrode. The conductive fabric is joined to one surface of the non-woven fabric by at least one of fusion and seaming.

19 Claims, 28 Drawing Sheets

(51) Int. Cl.

| | | |
|---|---|---|
| *B32B 5/06* | (2006.01) | |
| *B32B 5/26* | (2006.01) | |
| *B32B 7/025* | (2019.01) | |
| *B32B 7/05* | (2019.01) | |
| *B32B 7/09* | (2019.01) | |
| *B60N 2/00* | (2006.01) | |
| *B32B 5/02* | (2006.01) | |
| *A61B 5/00* | (2006.01) | |
| *A61B 5/27* | (2021.01) | |
| *B32B 37/00* | (2006.01) | |
| *B60R 21/015* | (2006.01) | |
| *A61B 5/11* | (2006.01) | |
| *B29C 65/00* | (2006.01) | |
| *B29C 65/02* | (2006.01) | |
| *B29C 65/72* | (2006.01) | |

(52) U.S. Cl.
CPC ... *A61B 2562/046* (2013.01); *A61B 2562/125* (2013.01); *B29C 65/02* (2013.01); *B29C 65/72* (2013.01); *B29C 66/242* (2013.01); *B29C 66/433* (2013.01); *B29C 66/729* (2013.01); *B29C 66/7292* (2013.01); *B29C 66/7294* (2013.01); *B29C 66/73141* (2013.01); *B29C 66/73143* (2013.01); *B32B 5/275* (2021.05); *B32B 5/277* (2021.05); *B32B 5/279* (2021.05); *B32B 7/09* (2019.01); *B32B 2250/03* (2013.01); *B32B 2250/04* (2013.01); *B32B 2250/05* (2013.01); *B32B 2250/20* (2013.01); *B32B 2250/40* (2013.01); *B32B 2250/42* (2013.01); *B32B 2250/44* (2013.01); *B32B 2255/02* (2013.01); *B32B 2255/205* (2013.01); *B32B 2262/0276* (2013.01); *B32B 2305/20* (2013.01); *B32B 2307/202* (2013.01); *B32B 2307/206* (2013.01); *B32B 2307/724* (2013.01); *B32B 2457/00* (2013.01); *B32B 2601/00* (2013.01); *B32B 2605/003* (2013.01); *B60R 21/01524* (2014.10); *Y10T 428/23* (2015.01); *Y10T 428/24033* (2015.01); *Y10T 428/2476* (2015.01); *Y10T 428/24777* (2015.01); *Y10T 428/24785* (2015.01); *Y10T 428/24793* (2015.01); *Y10T 428/24942* (2015.01); *Y10T 442/2418* (2015.04); *Y10T 442/339* (2015.04); *Y10T 442/3463* (2015.04); *Y10T 442/3707* (2015.04); *Y10T 442/419* (2015.04); *Y10T 442/494* (2015.04); *Y10T 442/655* (2015.04); *Y10T 442/659* (2015.04)

(56) References Cited

U.S. PATENT DOCUMENTS

| | | | | |
|---|---|---|---|---|
| 2002/0067064 A1* | 6/2002 | Jaillet | ............... | B60N 2/002 297/452.27 |
| 2003/0151240 A1* | 8/2003 | Saitou | ............... | B60R 21/01532 280/735 |
| 2003/0164715 A1* | 9/2003 | Lester | ............... | B60R 21/01516 324/661 |
| 2005/0235482 A1* | 10/2005 | Deaett | ............... | H01P 11/00 343/700 MS |
| 2006/0231320 A1* | 10/2006 | Kamizono | ............... | B60N 2/58 177/144 |
| 2007/0056493 A1* | 3/2007 | Burkitt | ............... | B32B 5/08 112/401 |
| 2007/0139275 A1* | 6/2007 | Deaett | ............... | H01Q 1/38 343/700 MS |
| 2007/0246120 A1* | 10/2007 | Krobok | ............... | B60N 2/002 139/421 |
| 2007/0248799 A1* | 10/2007 | DeAngelis | ............... | G01L 1/146 428/209 |
| 2009/0051607 A1* | 2/2009 | Ellinger | ............... | B60N 2/002 343/897 |
| 2010/0103112 A1* | 4/2010 | Yoo | ............... | H01H 13/704 345/169 |
| 2010/0147562 A1* | 6/2010 | Chu | ............... | B32B 27/02 156/92 |
| 2014/0084045 A1* | 3/2014 | Yang | ............... | A61B 5/6804 112/475.08 |
| 2016/0107551 A1* | 4/2016 | Nii | ............... | B60N 2/5642 297/452.47 |
| 2016/0192881 A1* | 7/2016 | Oehler | ............... | A61B 5/25 156/256 |
| 2016/0231098 A1* | 8/2016 | Otaka | ............... | G01B 7/22 |

FOREIGN PATENT DOCUMENTS

| | | | | |
|---|---|---|---|---|
| DE | 202004004182 U1 * | 9/2005 | ............. | A47C 7/748 |
| DE | 102006027213 A1 * | 12/2007 | ............. | H03K 17/962 |
| DE | 102008049112 A1 * | 5/2009 | ............. | A61B 5/04284 |
| DE | 102010023369 A1 * | 12/2010 | ............. | A61B 5/0408 |
| DE | 102009059113 A1 * | 6/2011 | ............. | B60N 2/002 |
| EP | 1927825 A1 * | 6/2008 | ............. | B60R 21/01532 |
| JP | 2000311564 A * | 11/2000 | | |
| JP | 2001124861 A * | 5/2001 | | |
| JP | 2001159683 A * | 6/2001 | | |
| JP | 2010086930 A * | 4/2010 | | |
| JP | 2010250980 A * | 11/2010 | | |
| JP | 2013-188277 | 9/2013 | | |
| JP | 2013170963 A * | 9/2013 | | |
| JP | 2013188277 A * | 9/2013 | ............. | A47C 31/126 |
| JP | 2014-193195 | 10/2014 | | |
| JP | 2016-182755 | 10/2016 | | |
| JP | 2018-21766 | 2/2018 | | |
| JP | 2018-102404 | 7/2018 | | |
| KR | 10-2017-0077514 | 7/2017 | | |
| KR | 2017077514 A * | 7/2017 | ............. | A47C 31/126 |
| LU | 91866 B1 * | 3/2013 | | |
| WO | WO-2008148713 A2 * | 12/2008 | ............. | B60N 2/002 |
| WO | WO-2014204323 A1 * | 12/2014 | ............. | A41D 1/002 |
| WO | 2015/099040 | 7/2015 | | |

OTHER PUBLICATIONS

Machine Translation of DE-102008049112-A1, May 2009 (Year: 2009).*
Machine Translation of DE-19826391-A1, Dec. 1999 (Year: 1999).*
Machine Translation of JP-2013188277-A, Sep. 2013 (Year: 2013).*
Machine Translation of KR-2017077514-A, Jul. 2017 (Year: 2017).*
International Search Report from International Application No. PCT/JP2018/044077 dated Mar. 5, 2019.

* cited by examiner

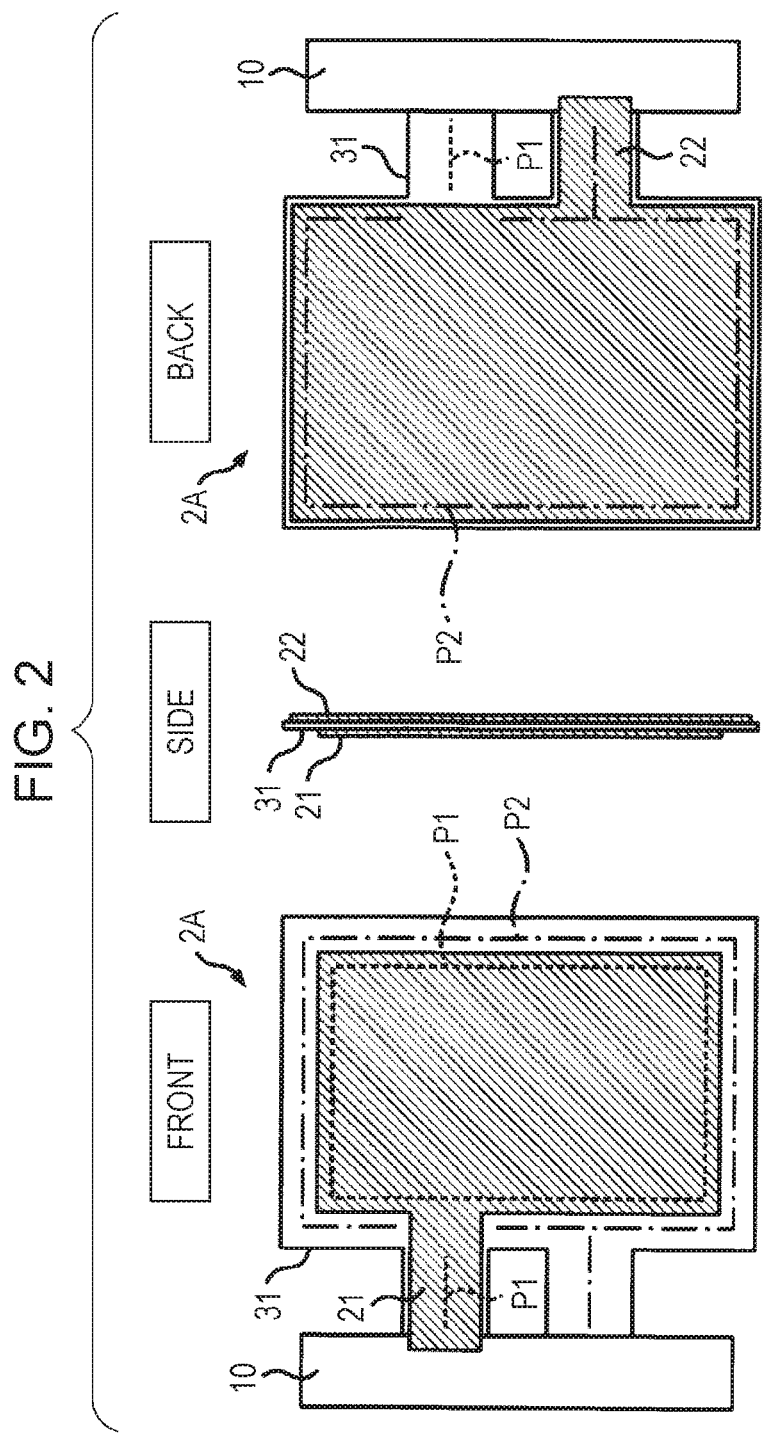

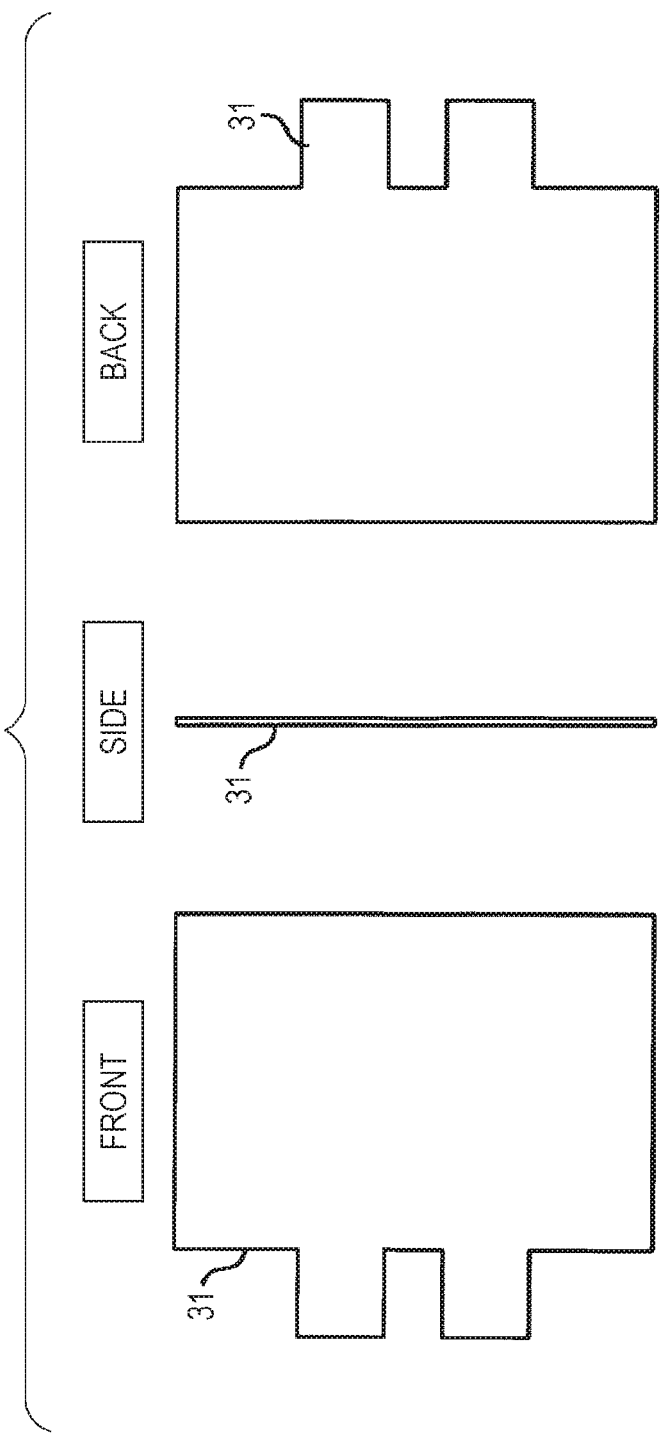

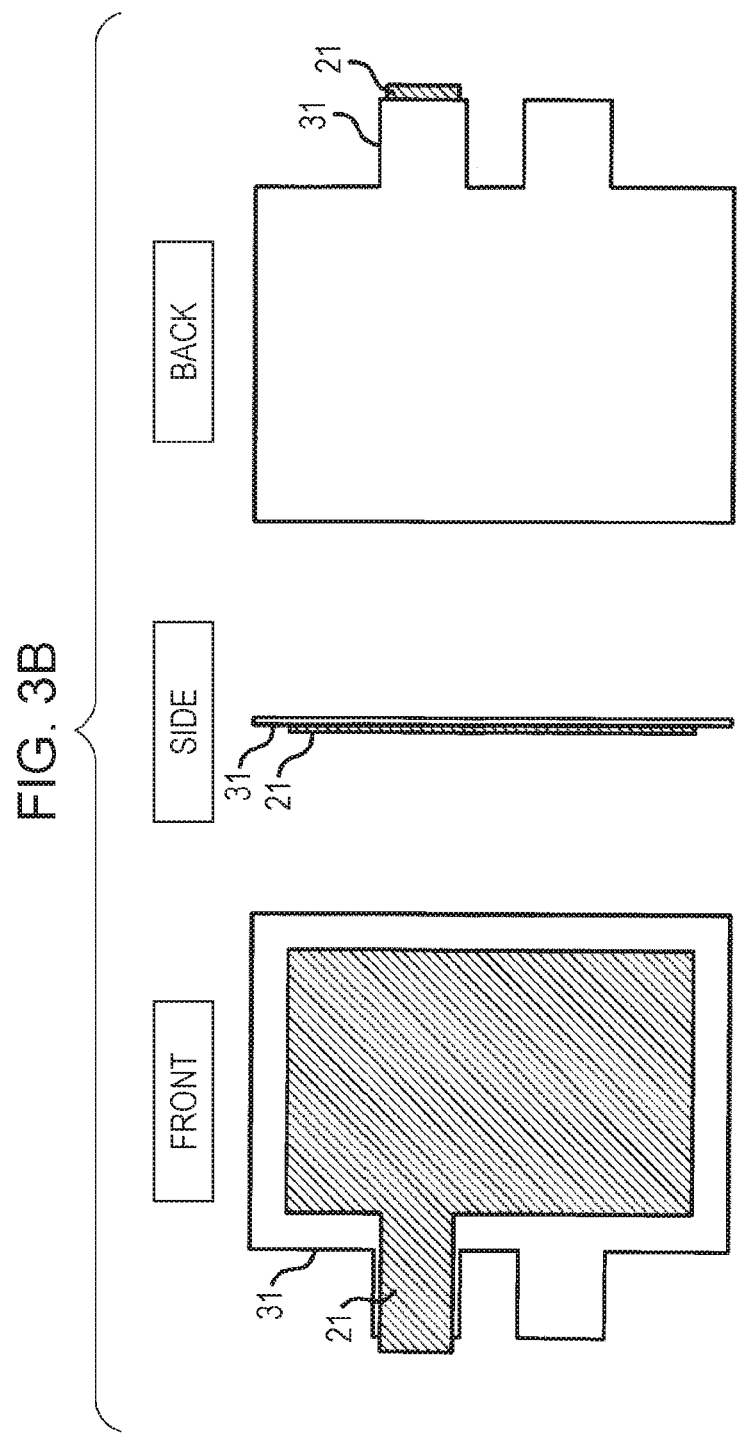

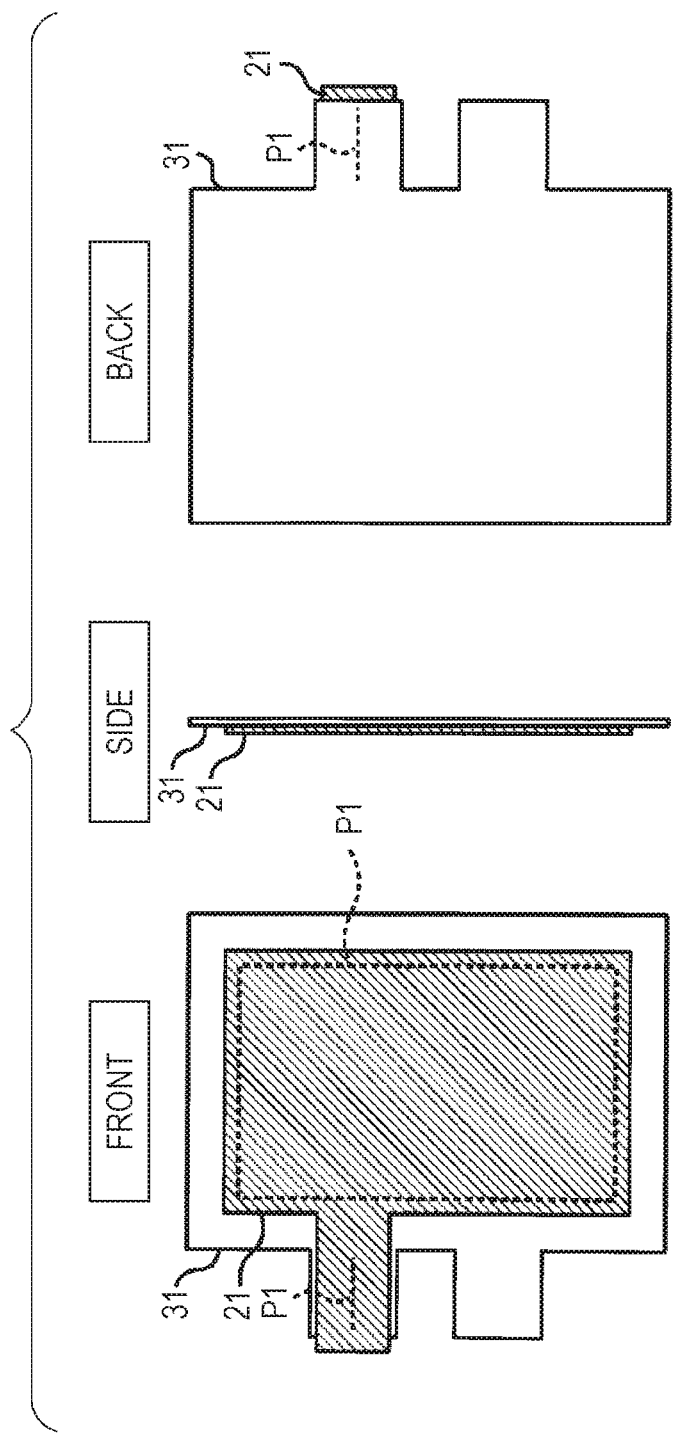

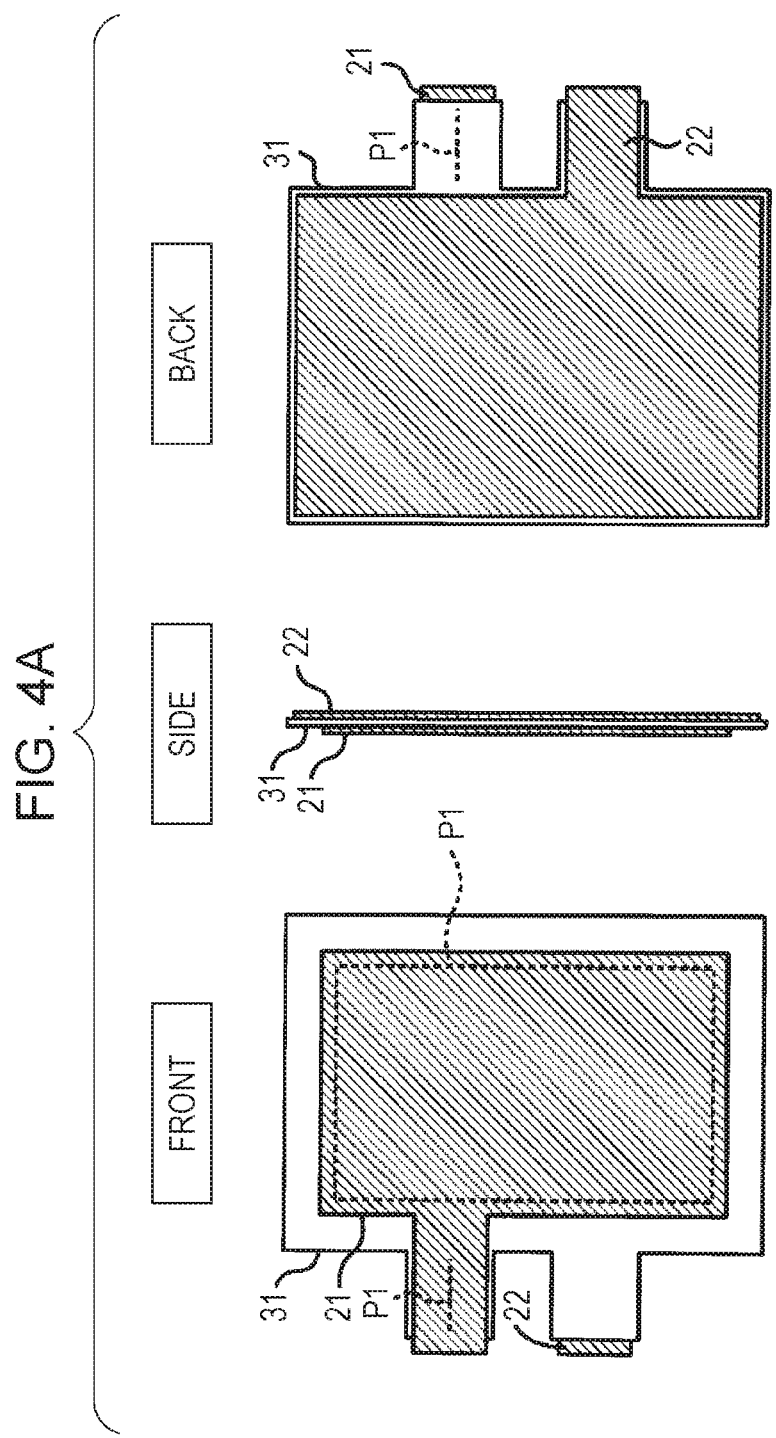

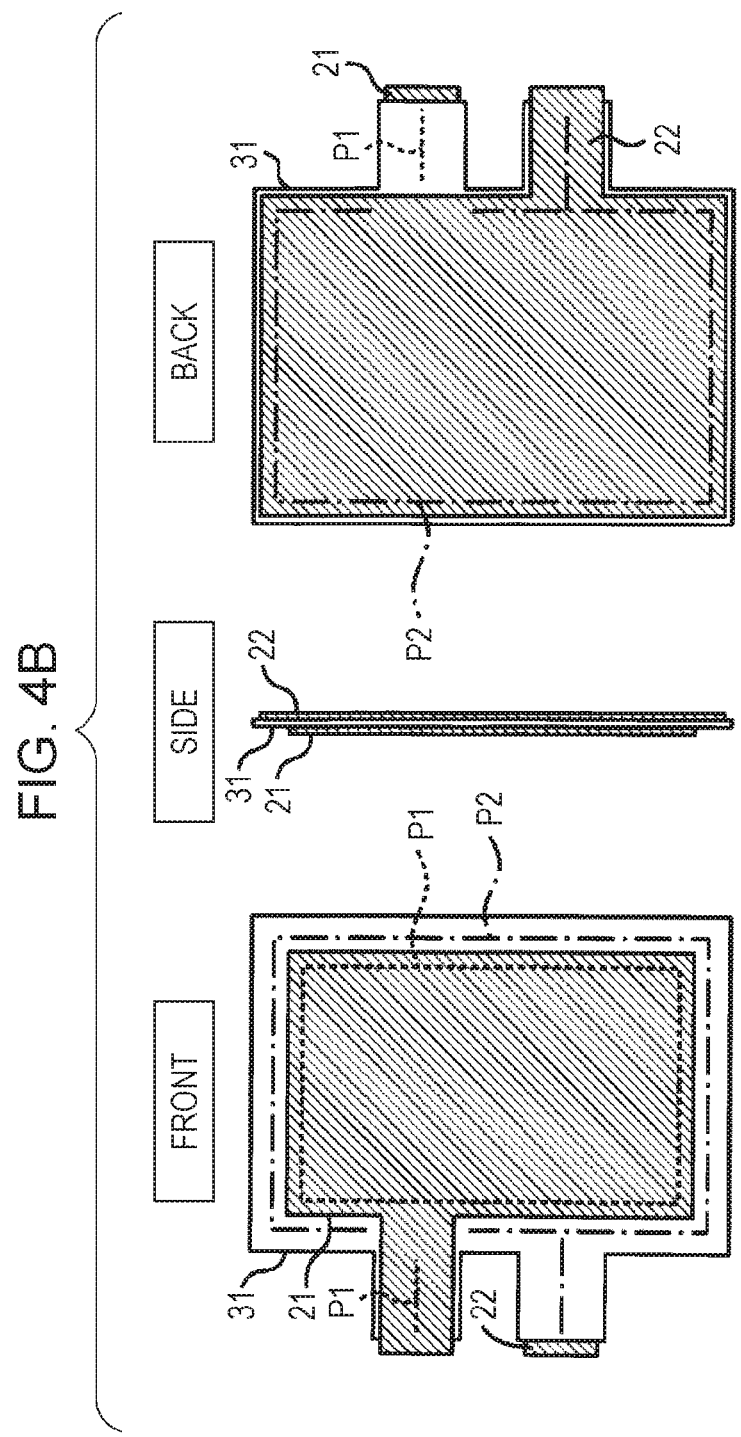

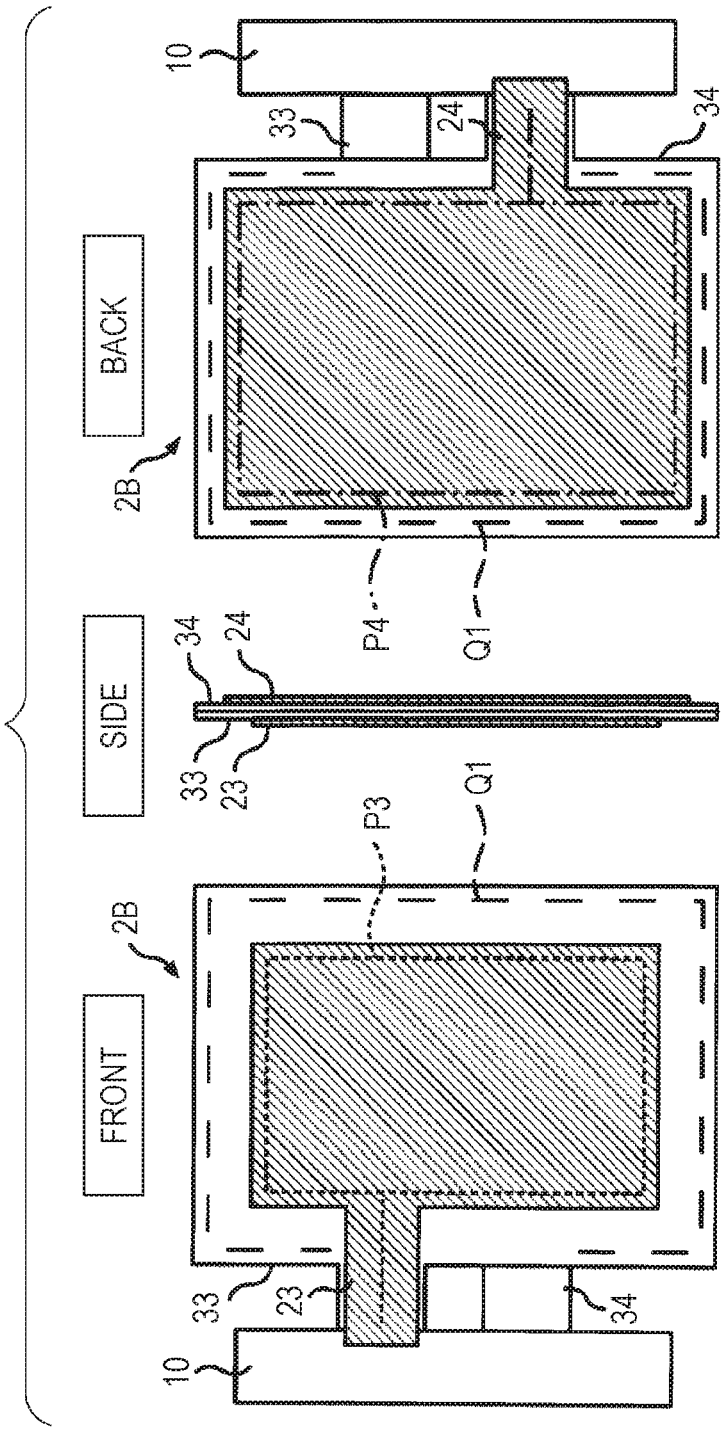

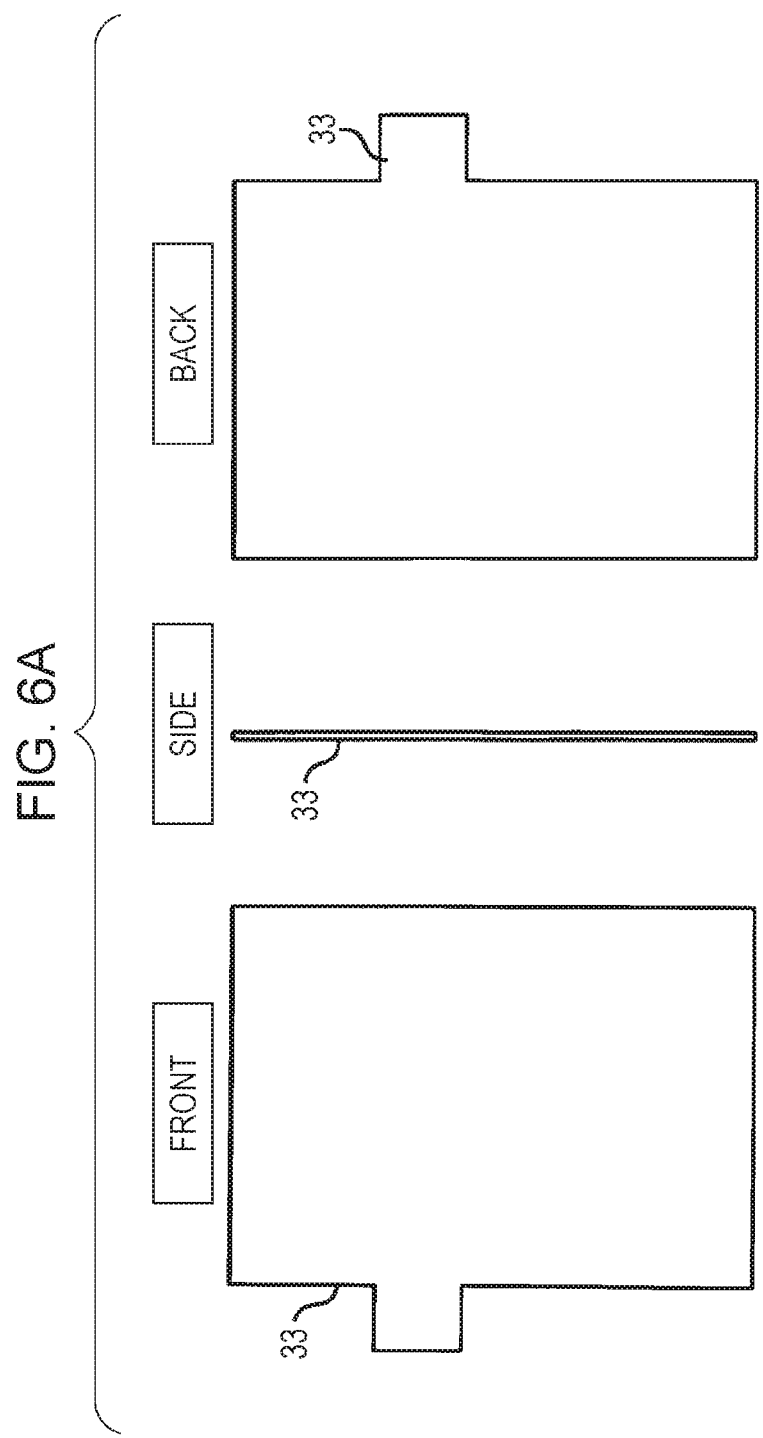

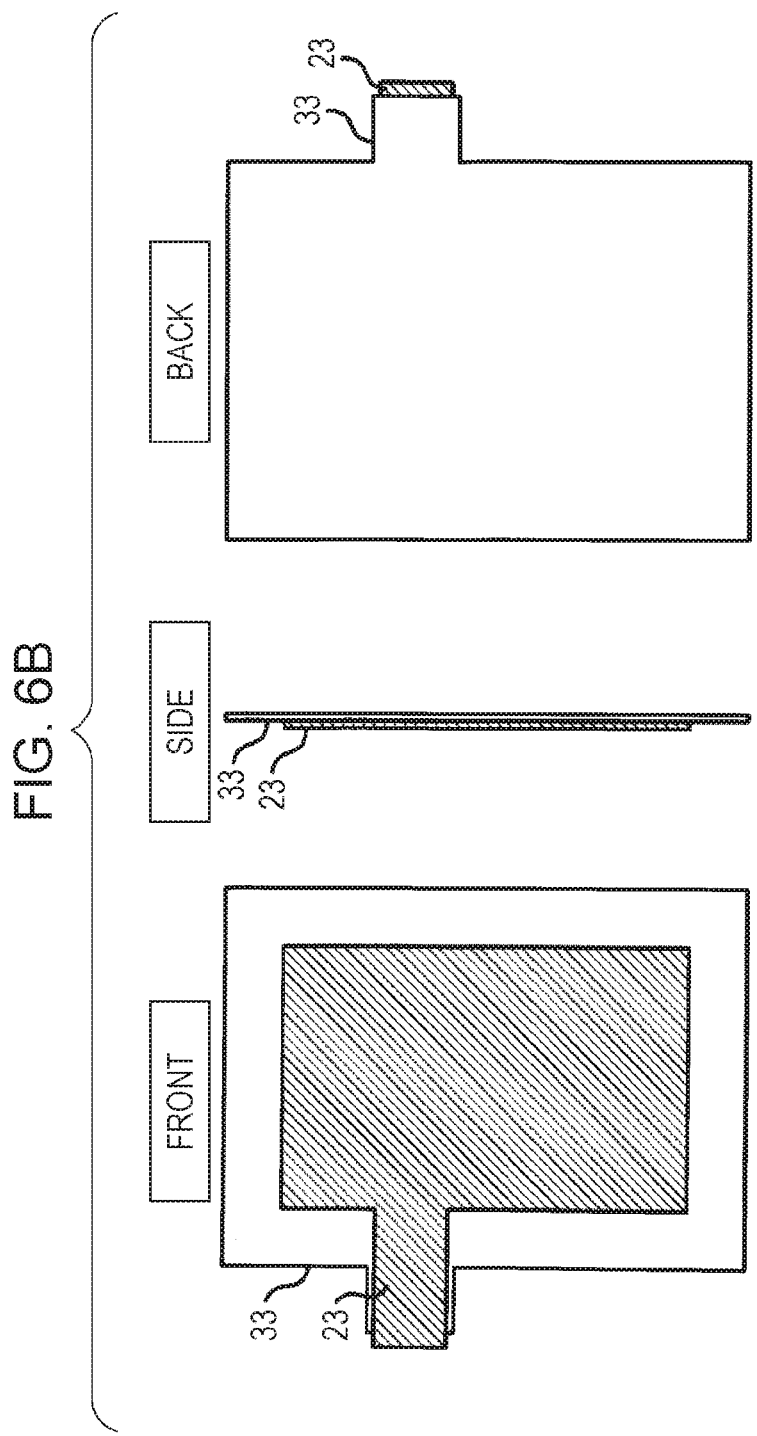

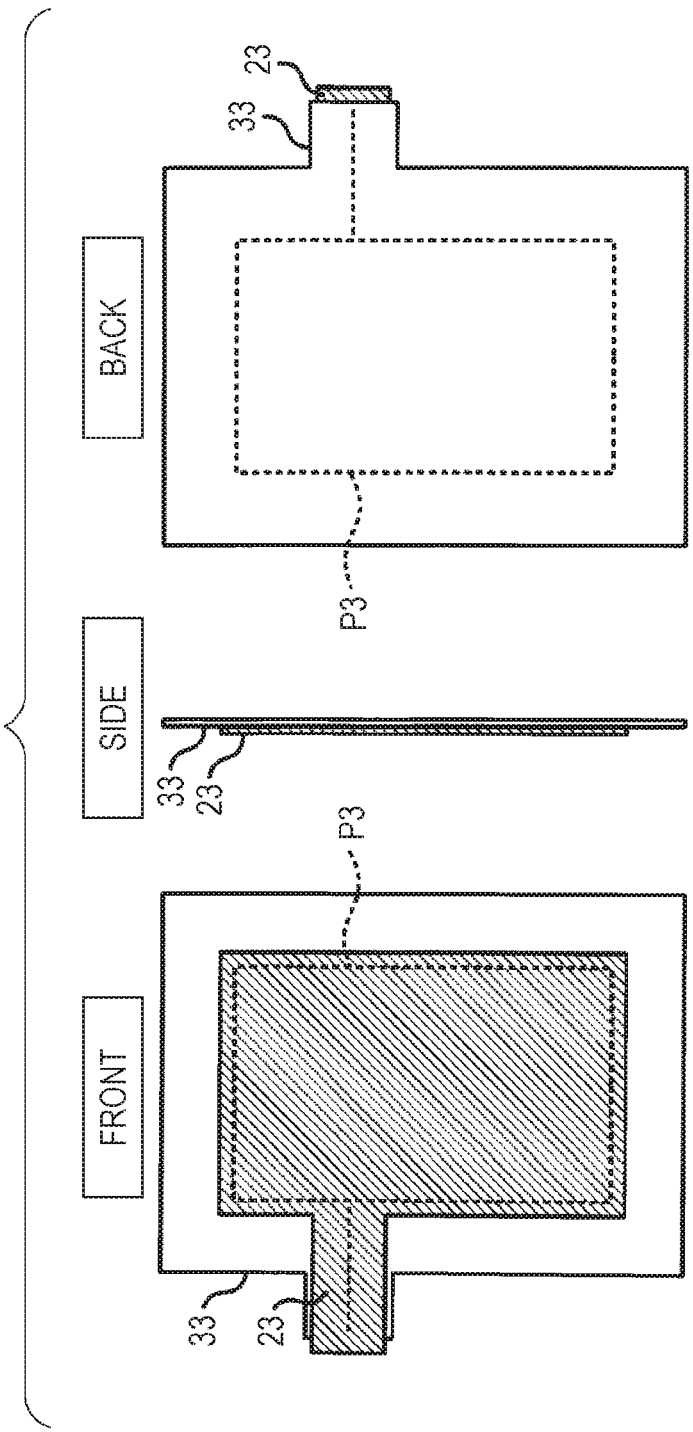

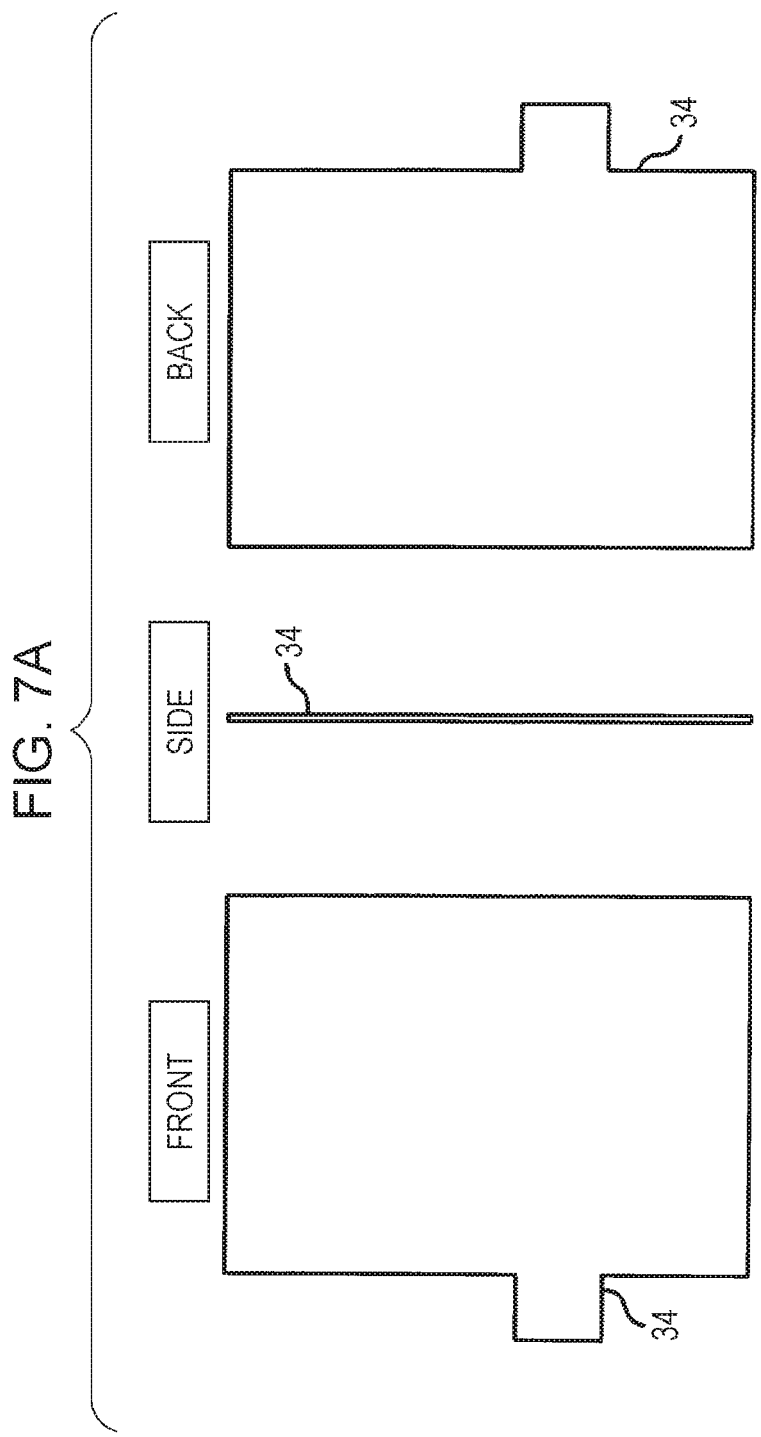

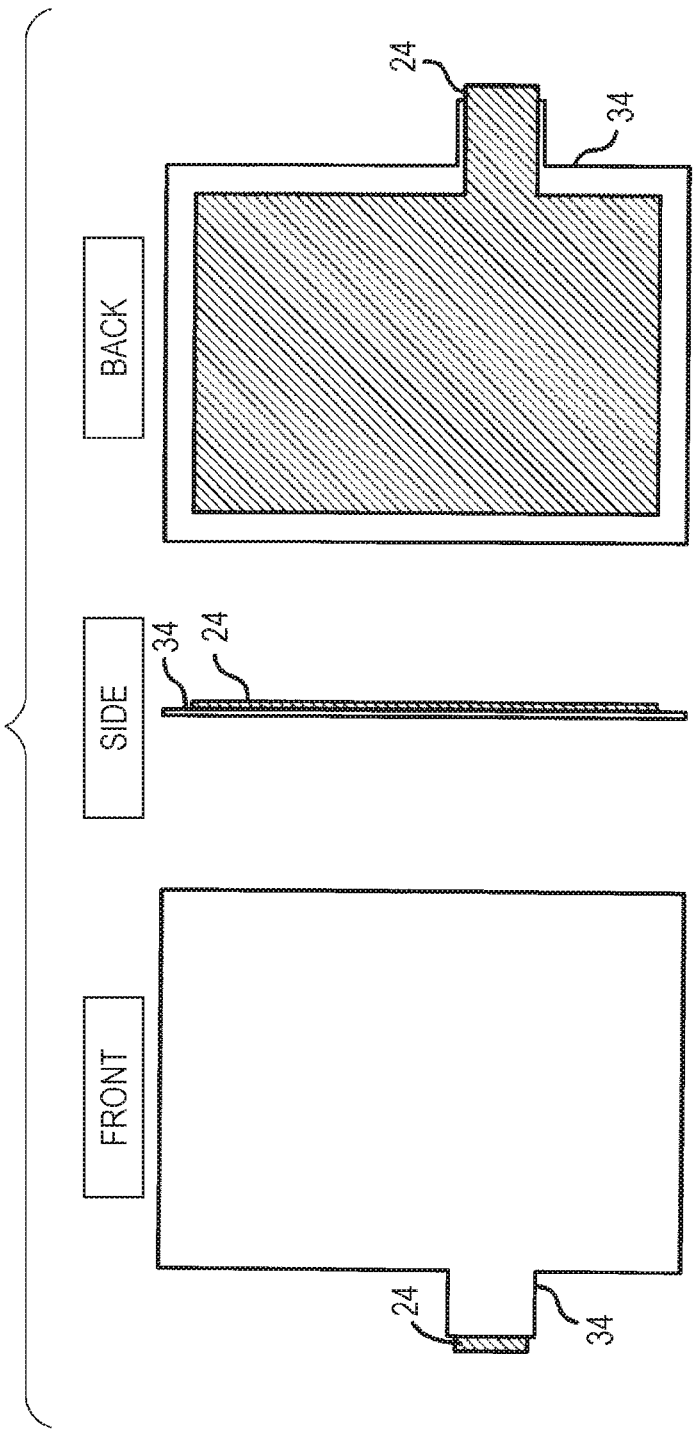

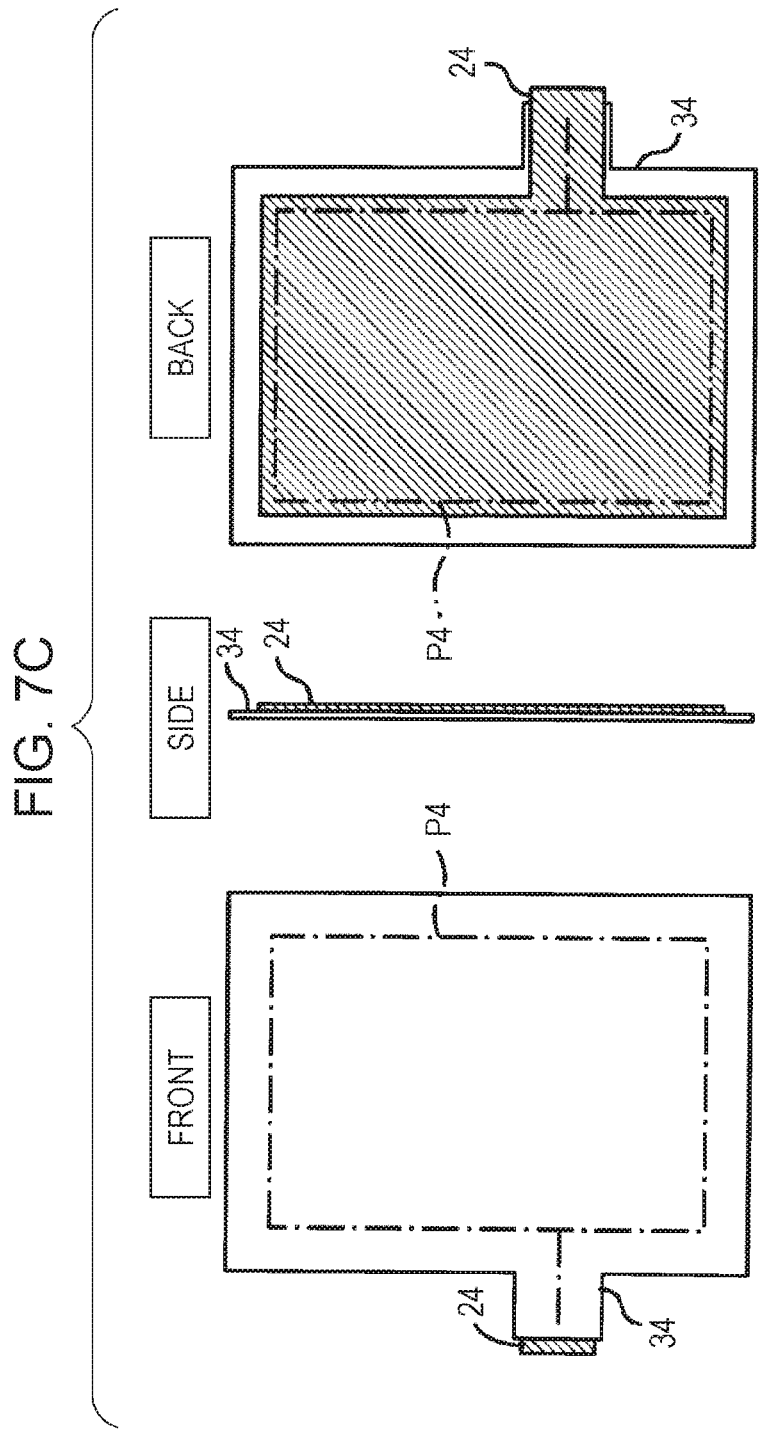

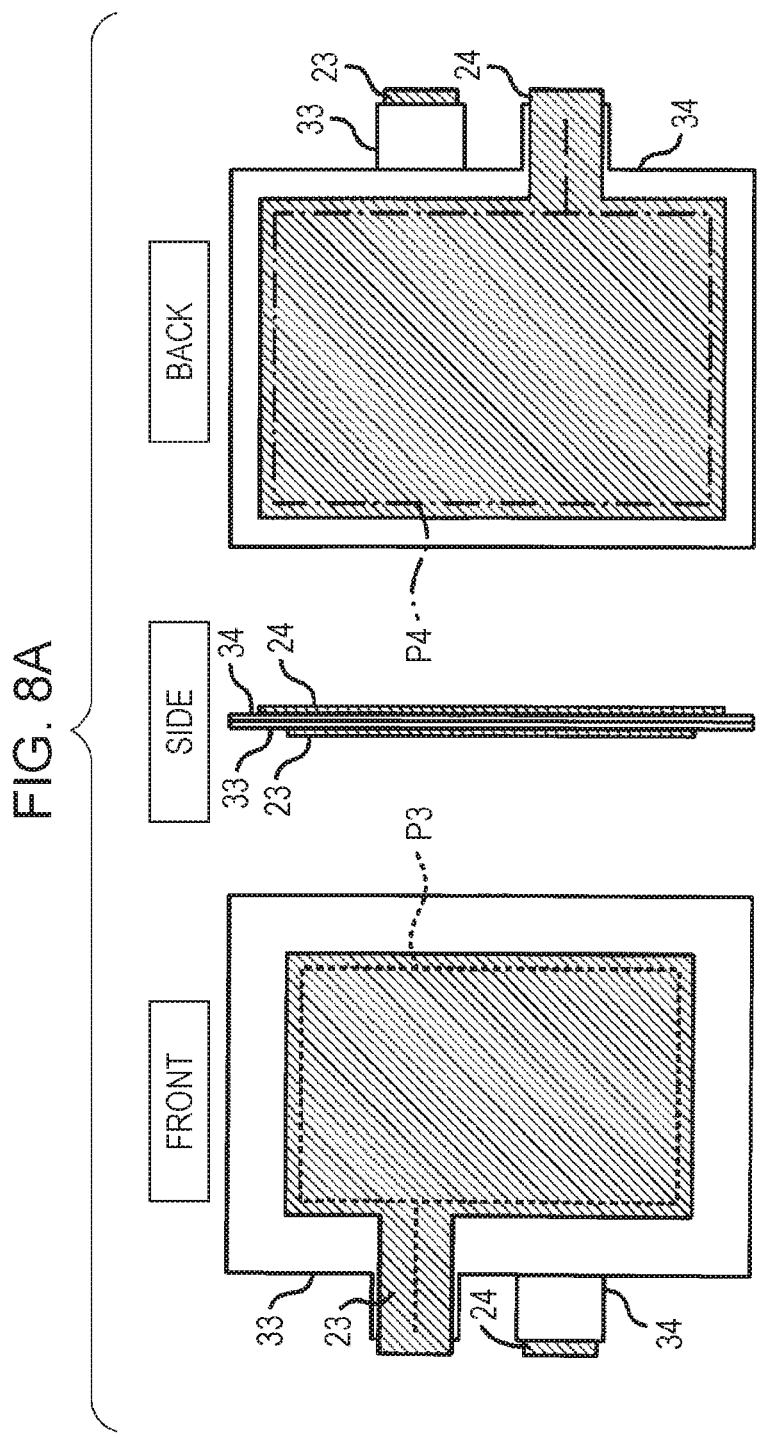

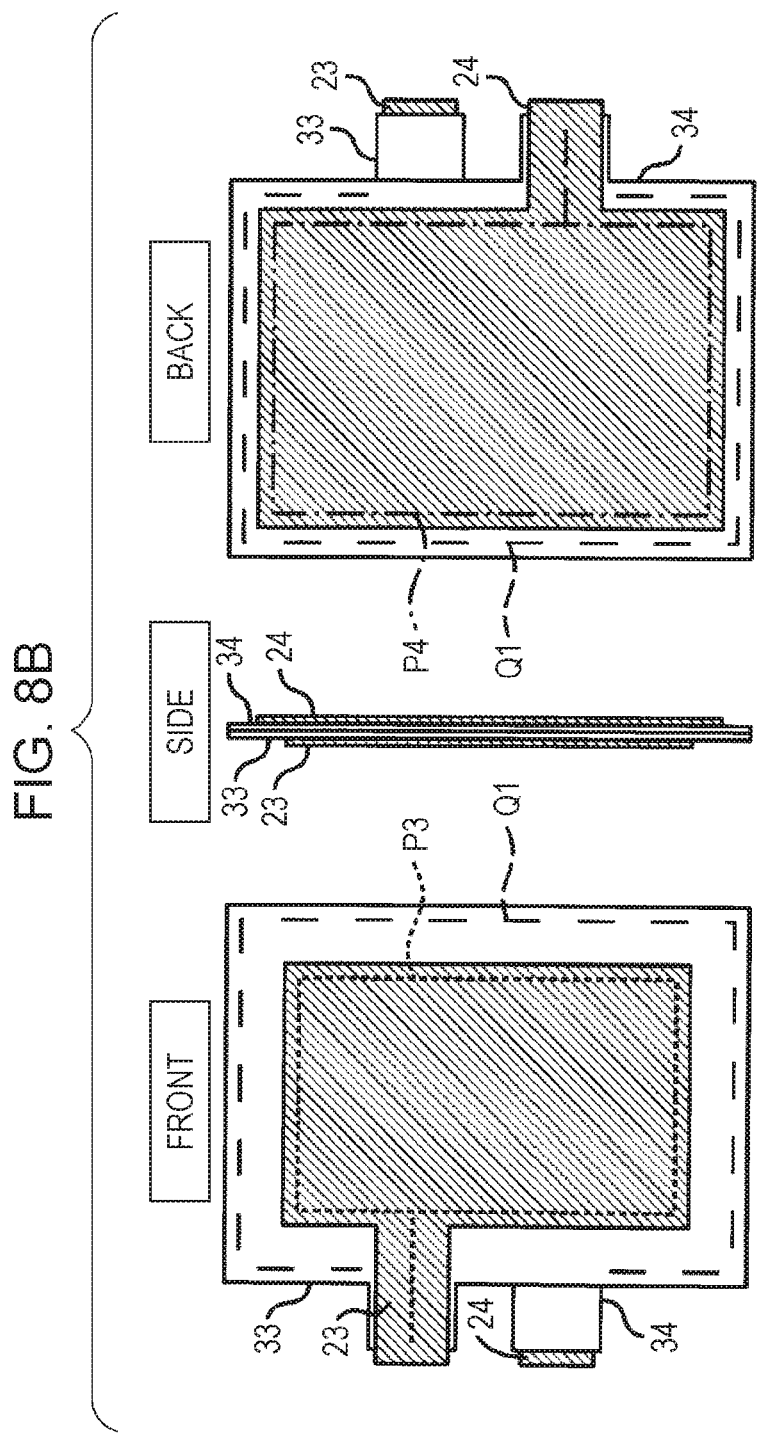

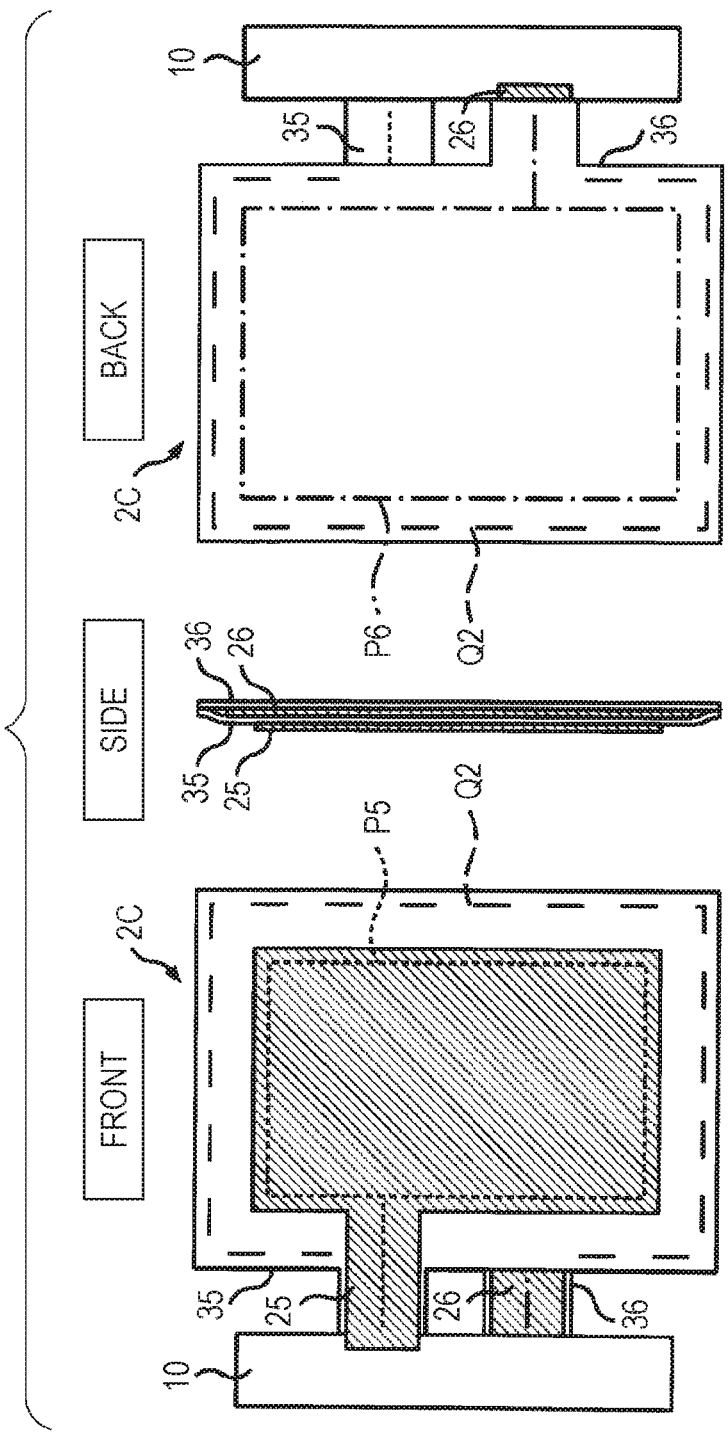

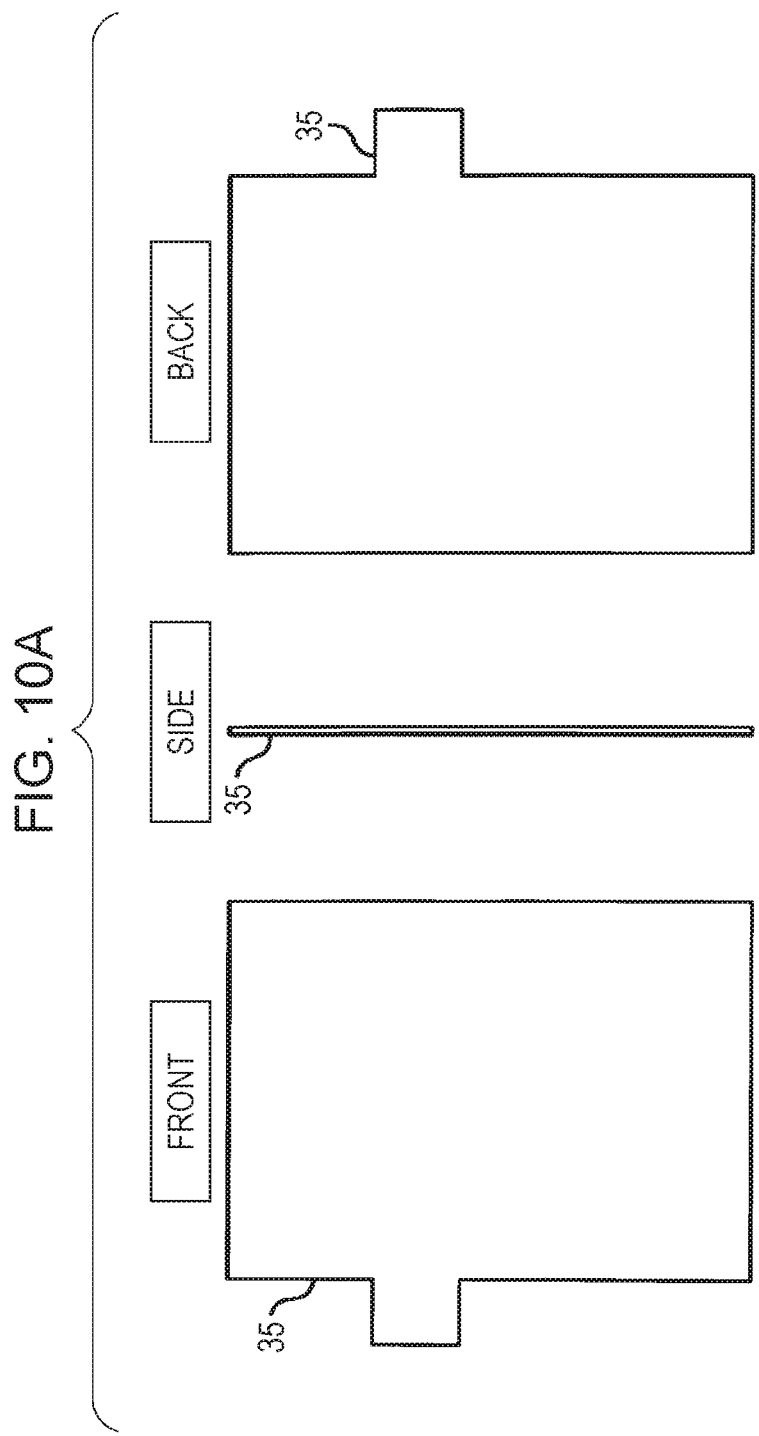

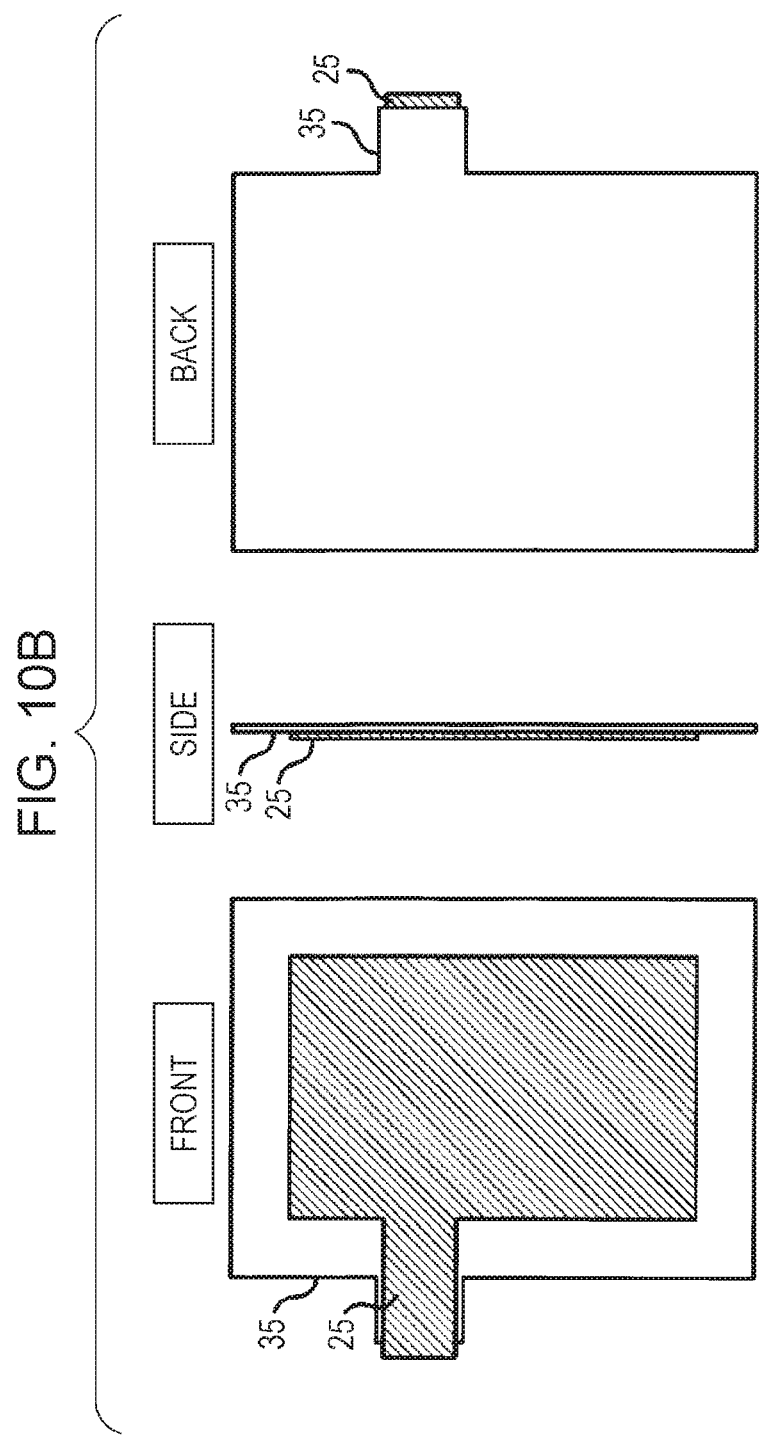

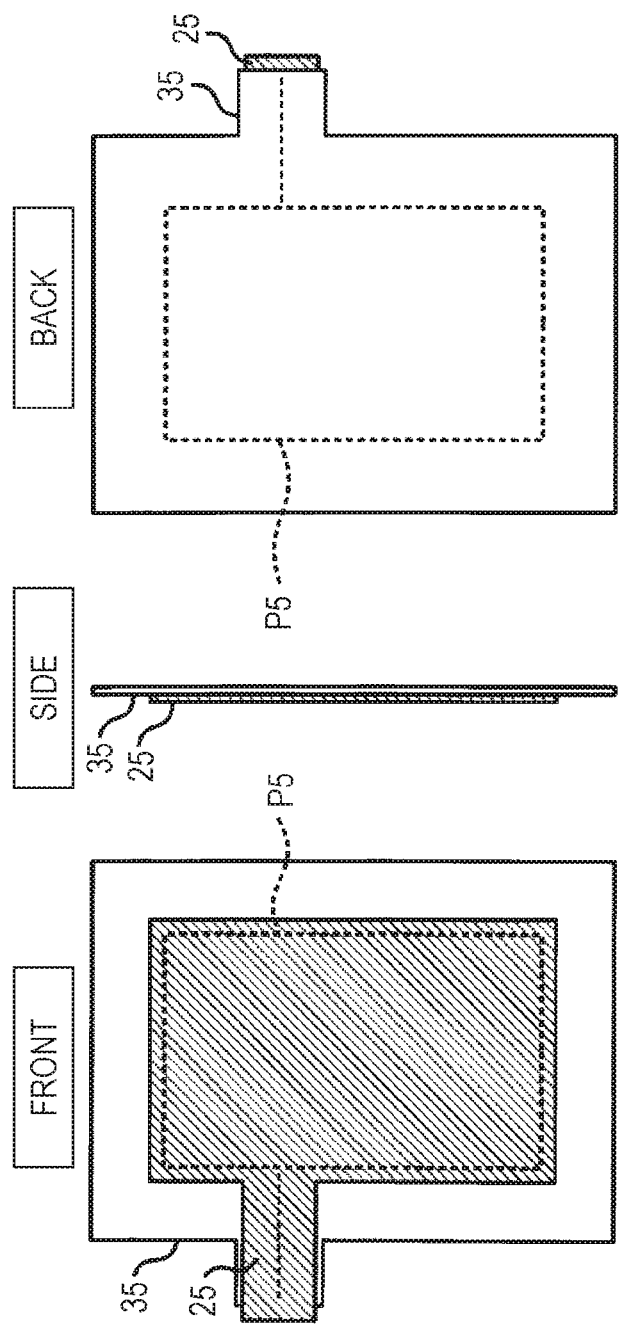

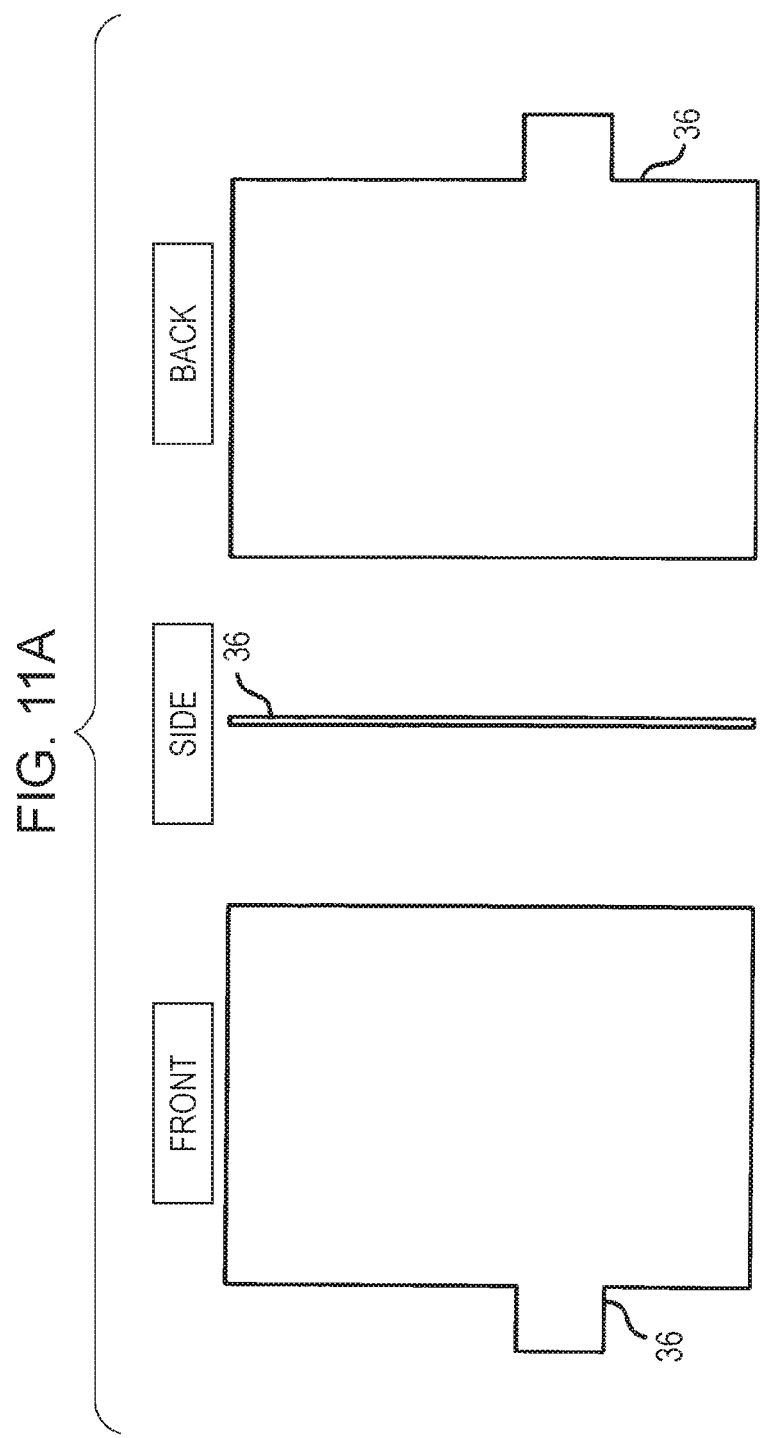

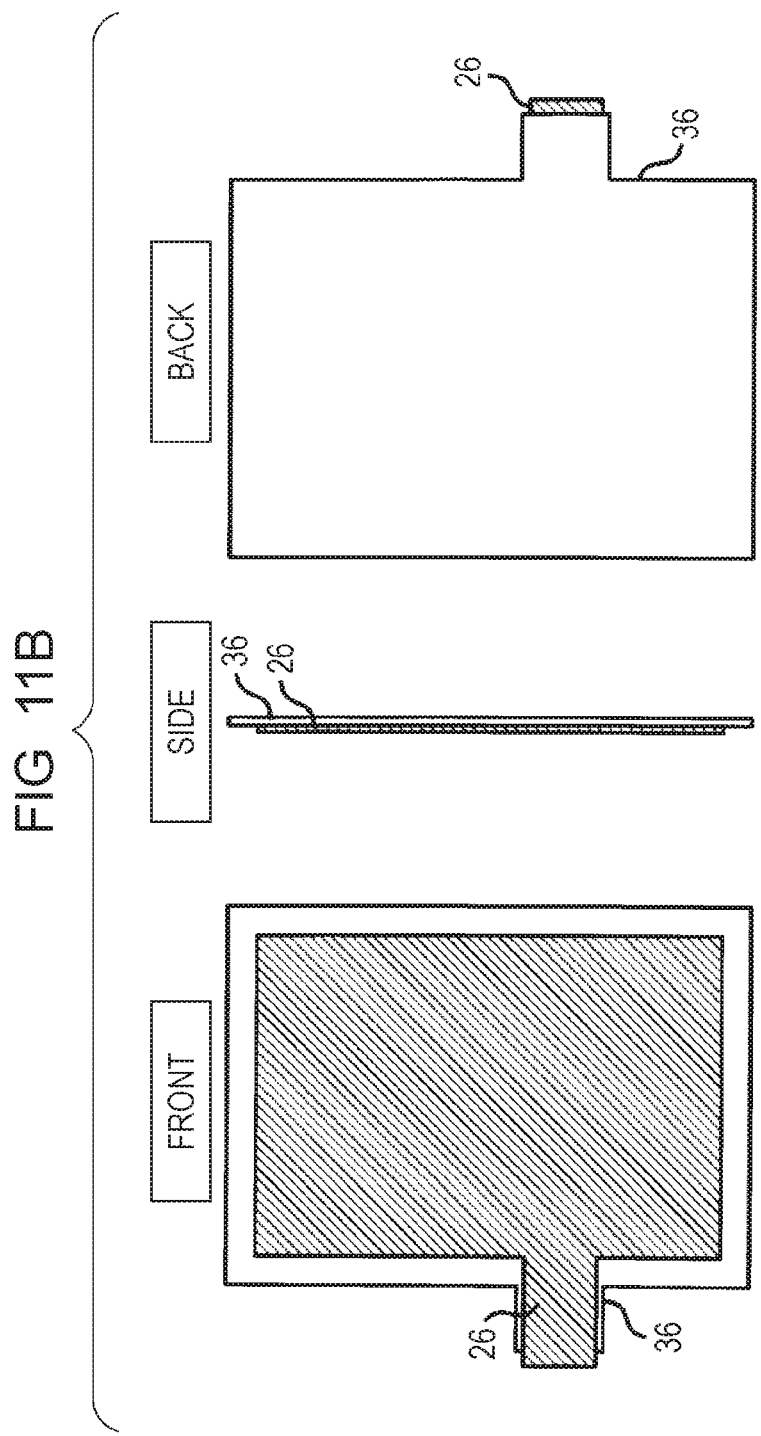

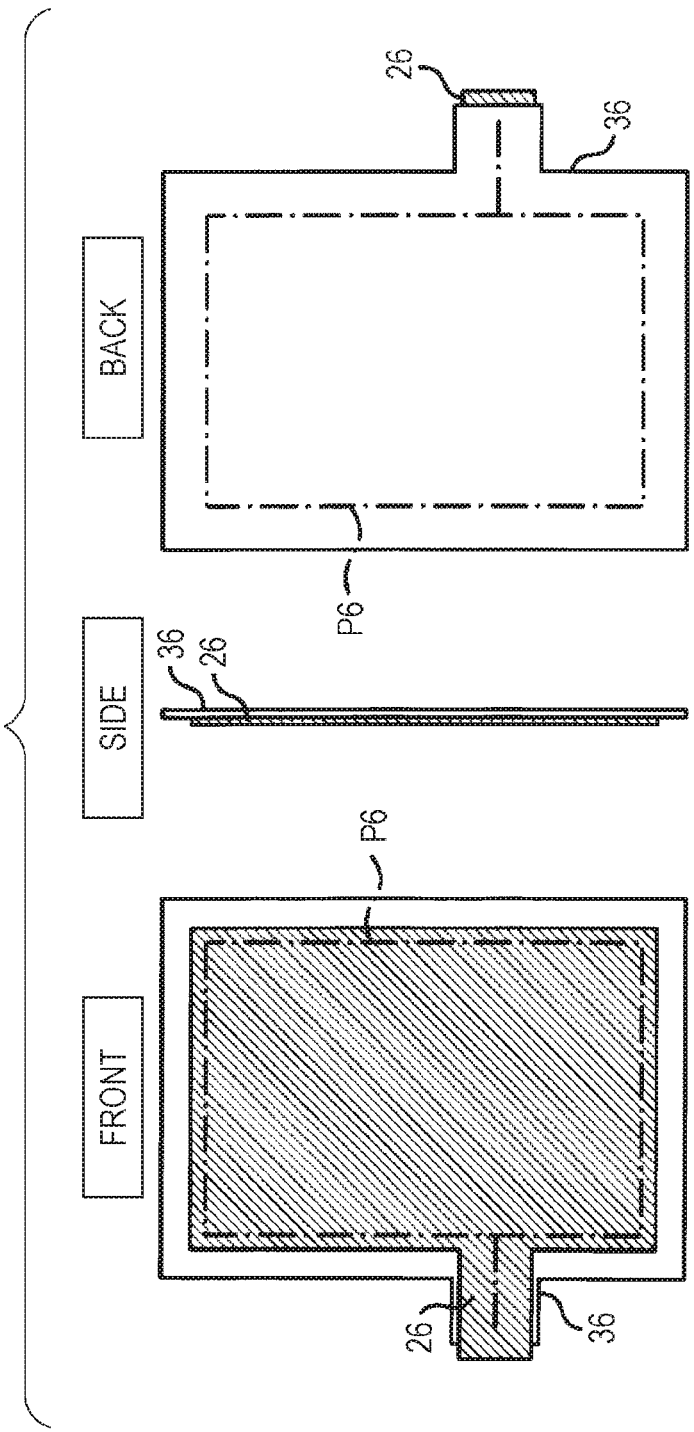

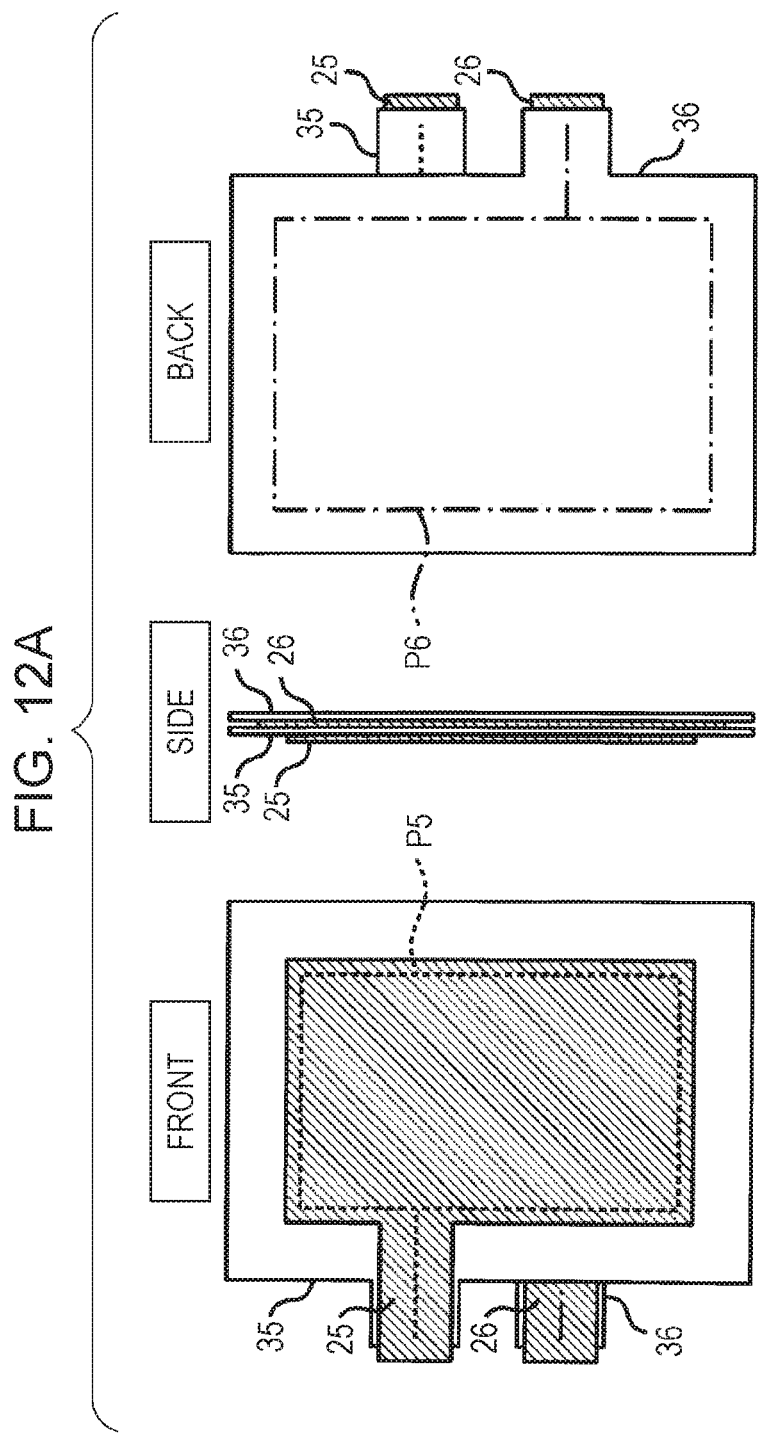

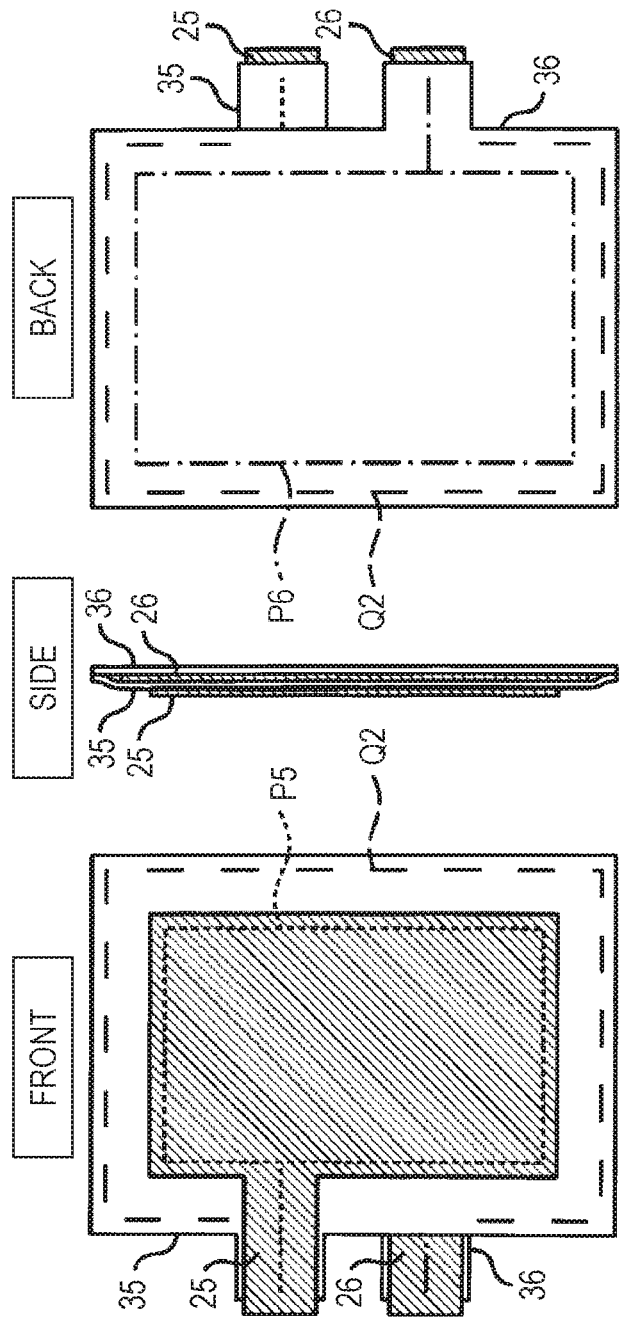

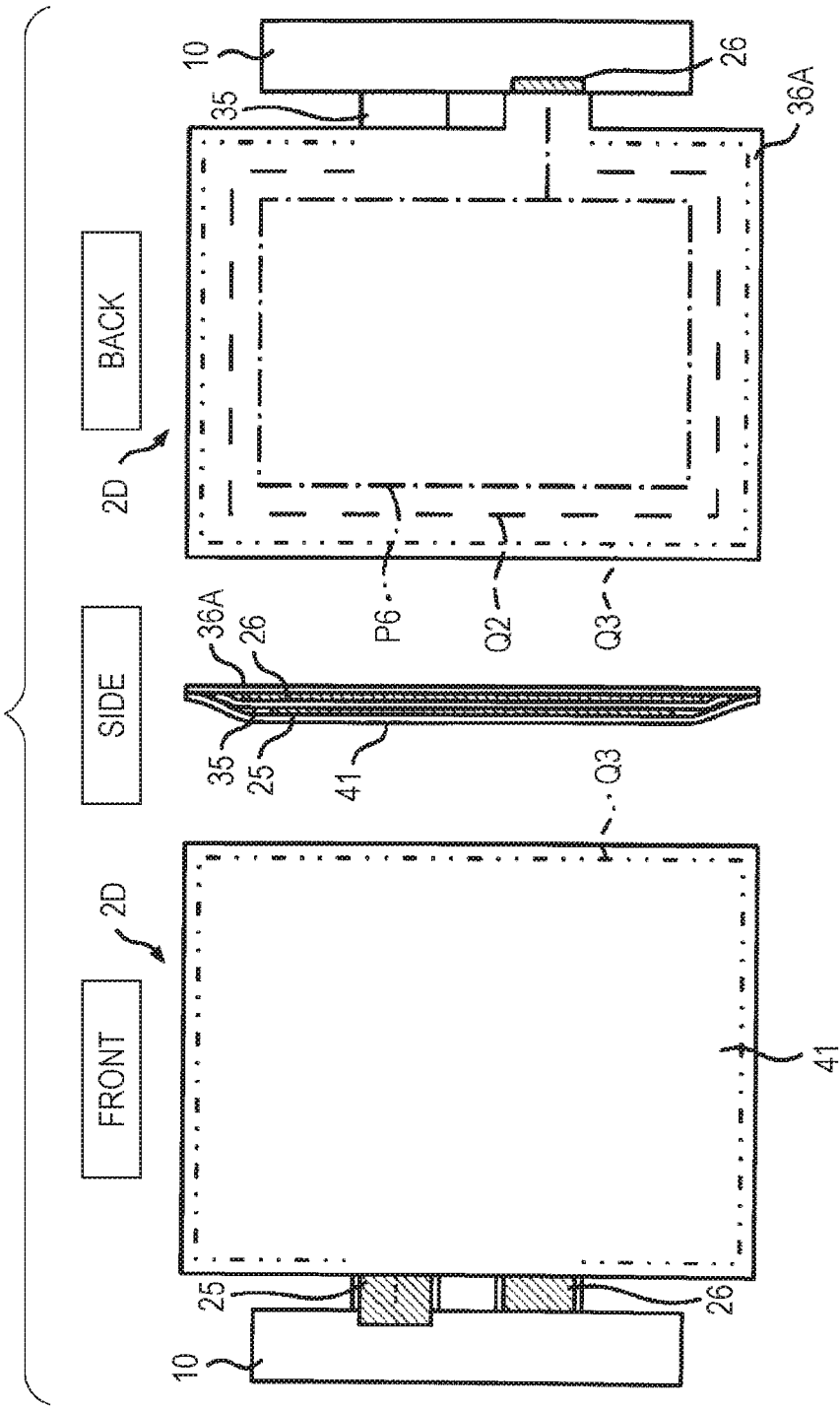

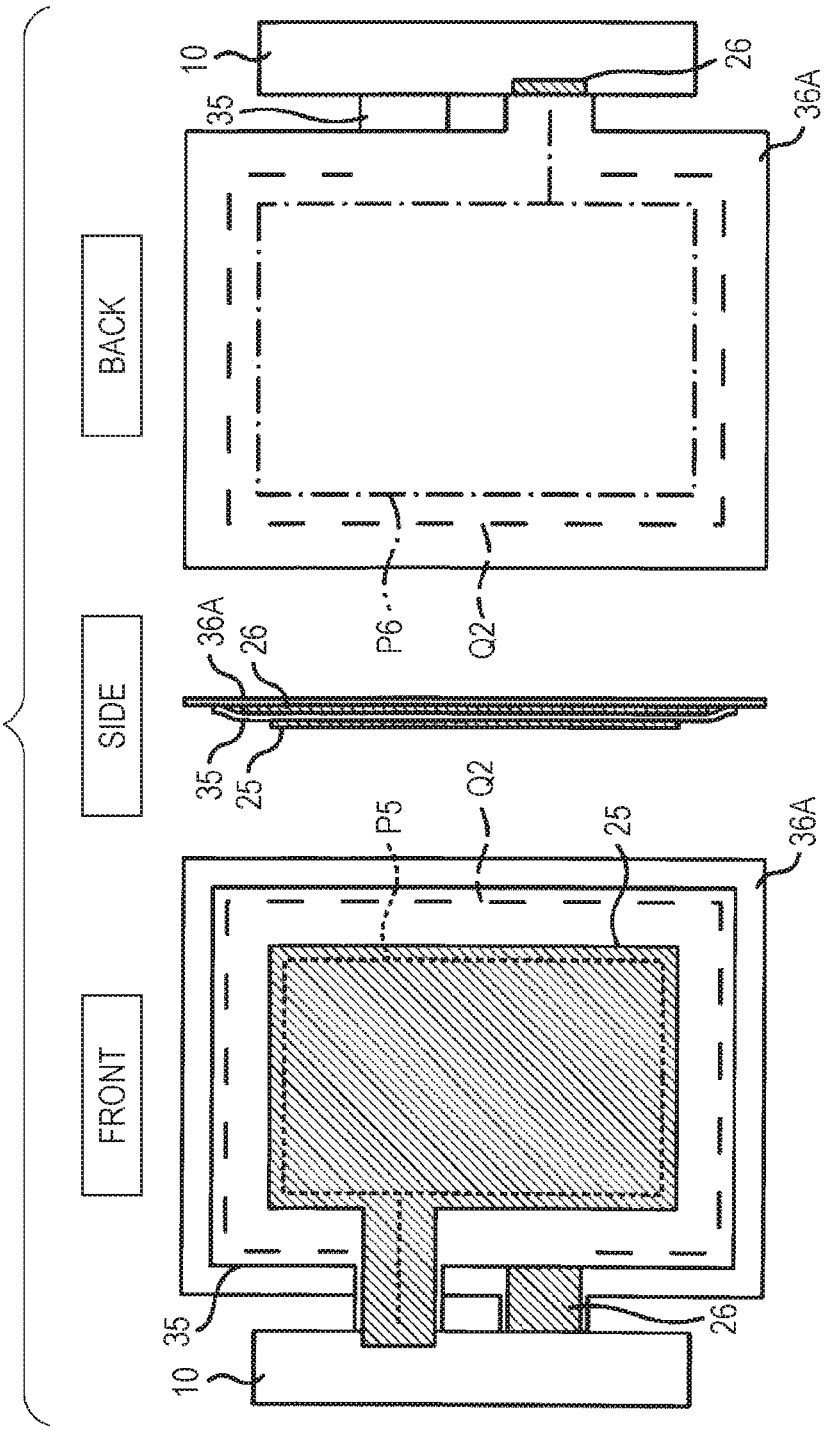

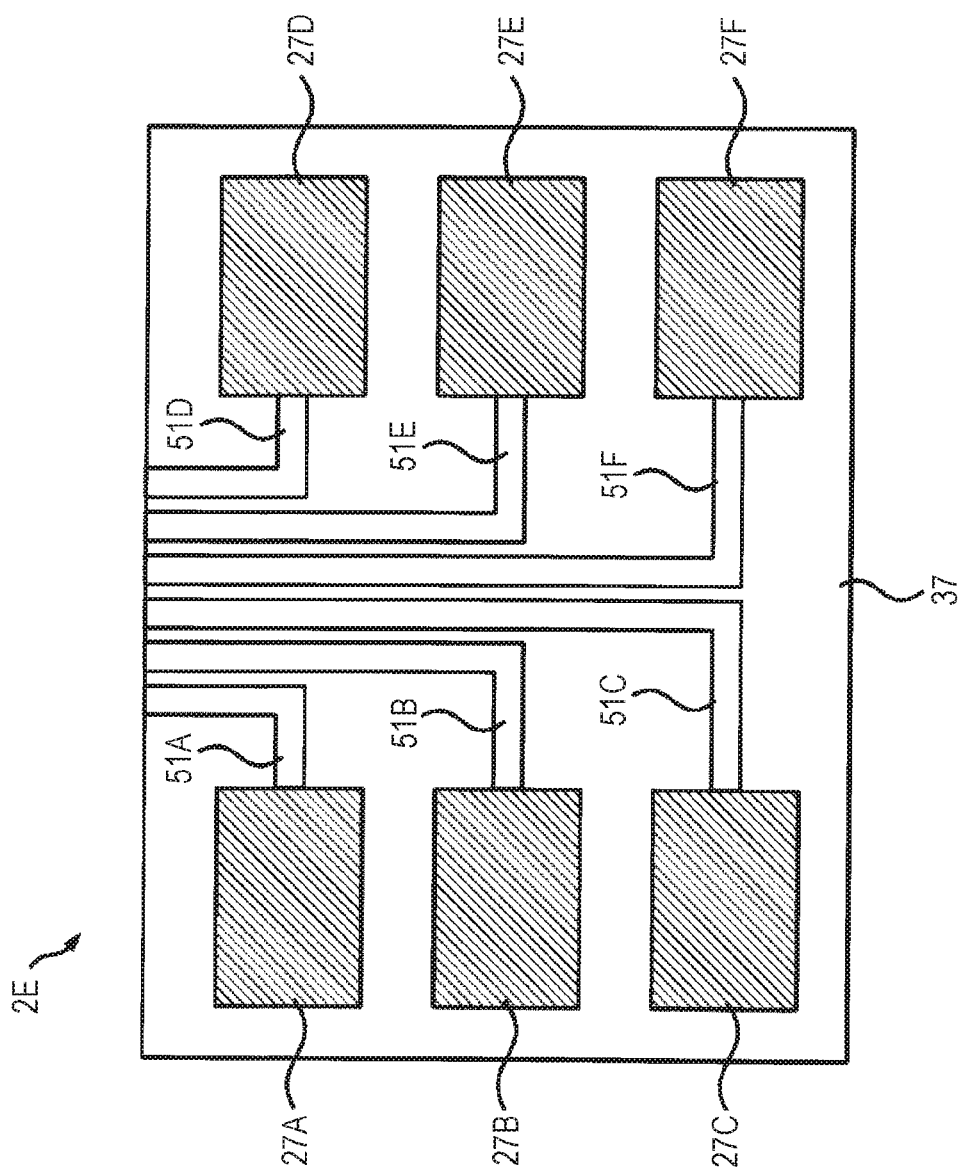

SENSOR DEVICE, METHOD OF MANUFACTURING SENSOR DEVICE, AND VEHICLE SEAT

CLAIM OF PRIORITY

This application is a Continuation of International Application No. PCT/JP2018/044077 filed on Nov. 29, 2018, which claims benefit of Japanese Patent Application No. 2017-241148 filed on Dec. 15, 2017. The entire contents of each application noted above are hereby incorporated by reference.

BACKGROUND OF THE INVENTION

1. Field of the Invention

The present invention relates to a sensor device, a method of manufacturing the sensor device, and a vehicle seat equipped with a sensor device.

2. Description of the Related Art

A known device contactlessly detects a motion or electric phenomenon of a live body by using an electrode disposed near the live body. In Japanese Unexamined Patent Application Publication No. 2013-188277, for example, an electrode device is described that is disposed at a vehicle seat or the like and performs electrocardiogram measurement.

SUMMARY OF THE INVENTION

In the electrode device described in Japanese Unexamined Patent Application Publication No. 2013-188277, an electrode and insulating body are formed from a woven fabric or knitted fabric having stretchability and air permeability to suppress a feeling of discomfort in touch and a feeling of stuffiness when the electrode device is used at a vehicle seat or the like.

However, when the insulating body is formed from a woven fabric or knitted fabric, if part of the fabric ravels, the ravel easily expand to the periphery thereof. The insulation property decreases at the raveled portion. This may lead to a problem in detection performance.

In view of this, one aspect of the present disclosure provides a sensor device that can suppress a decrease in an insulation property for electrodes while maintaining air permeability and flexibility, a method of manufacturing the sensor device, and a vehicle seat using such sensor devices.

According to one aspect of the present disclosure, a sensor device that has an insulative non-woven fabric and a conductive fabric forming an electrode is provided. The conductive fabric is joined to one surface of the non-woven fabric by at least one of fusion and seaming.

One aspect of the present disclosure can provide a sensor device that can suppress a decrease in an insulation property for electrodes while maintaining air permeability and flexibility, a method of manufacturing the sensor device, and a vehicle seat using such sensor devices.

BRIEF DESCRIPTION OF THE DRAWINGS

FIG. 2 illustrates an example of a sensor device according to a first embodiment;

FIG. 3A illustrates an example of a method of manufacturing the sensor device in FIG. 2;

FIG. 3B illustrates the example of the method of manufacturing the sensor device in FIG. 2;

FIG. 3C illustrates the example of the method of manufacturing the sensor device in FIG. 2;

FIG. 4A illustrates an example of the method of manufacturing the sensor device in FIG. 2;

FIG. 4B illustrates an example of the method of manufacturing the sensor device in FIG. 2;

FIG. 5 illustrates an example of a sensor device according to a second embodiment;

FIG. 6A illustrates an example of a method of manufacturing the sensor device in FIG. 5;

FIG. 6B illustrates the example of the method of manufacturing the sensor device in FIG. 5;

FIG. 6C illustrates the example of the method of manufacturing the sensor device in FIG. 5;

FIG. 7A illustrates the example of the method of manufacturing the sensor device in FIG. 5;

FIG. 7B illustrates the example of the method of manufacturing the sensor device in FIG. 5;

FIG. 7C illustrates the example of the method of manufacturing the sensor device in FIG. 5;

FIG. 8A illustrates the example of the method of manufacturing the sensor device in FIG. 5;

FIG. 8B illustrates the example of the method of manufacturing the sensor device in FIG. 5;

FIG. 9 illustrates an example of a sensor device according to a third embodiment;

FIG. 10A illustrates an example of a method of manufacturing the sensor device in FIG. 9;

FIG. 10B illustrates the example of the method of manufacturing the sensor device in FIG. 9;

FIG. 10C illustrates the example of the method of manufacturing the sensor device in FIG. 9;

FIG. 11A illustrates the example of the method of manufacturing the sensor device in FIG. 9;

FIG. 11B illustrates the example of the method of manufacturing the sensor device in FIG. 9;

FIG. 11C illustrates the example of the method of manufacturing the sensor device in FIG. 9;

FIG. 12A illustrates the example of the method of manufacturing the sensor device in FIG. 9;

FIG. 12B illustrates the example of the method of manufacturing the sensor device in FIG. 9;

FIG. 13A illustrates an example of a sensor device according to a fourth embodiment;

FIG. 13B illustrates the sensor device in FIG. 13A, in a state in which the electrode cover is not illustrated; and FIG. 14 illustrates one variation of a sensor device.

DESCRIPTION OF THE PREFERRED EMBODIMENTS

Figure 1:
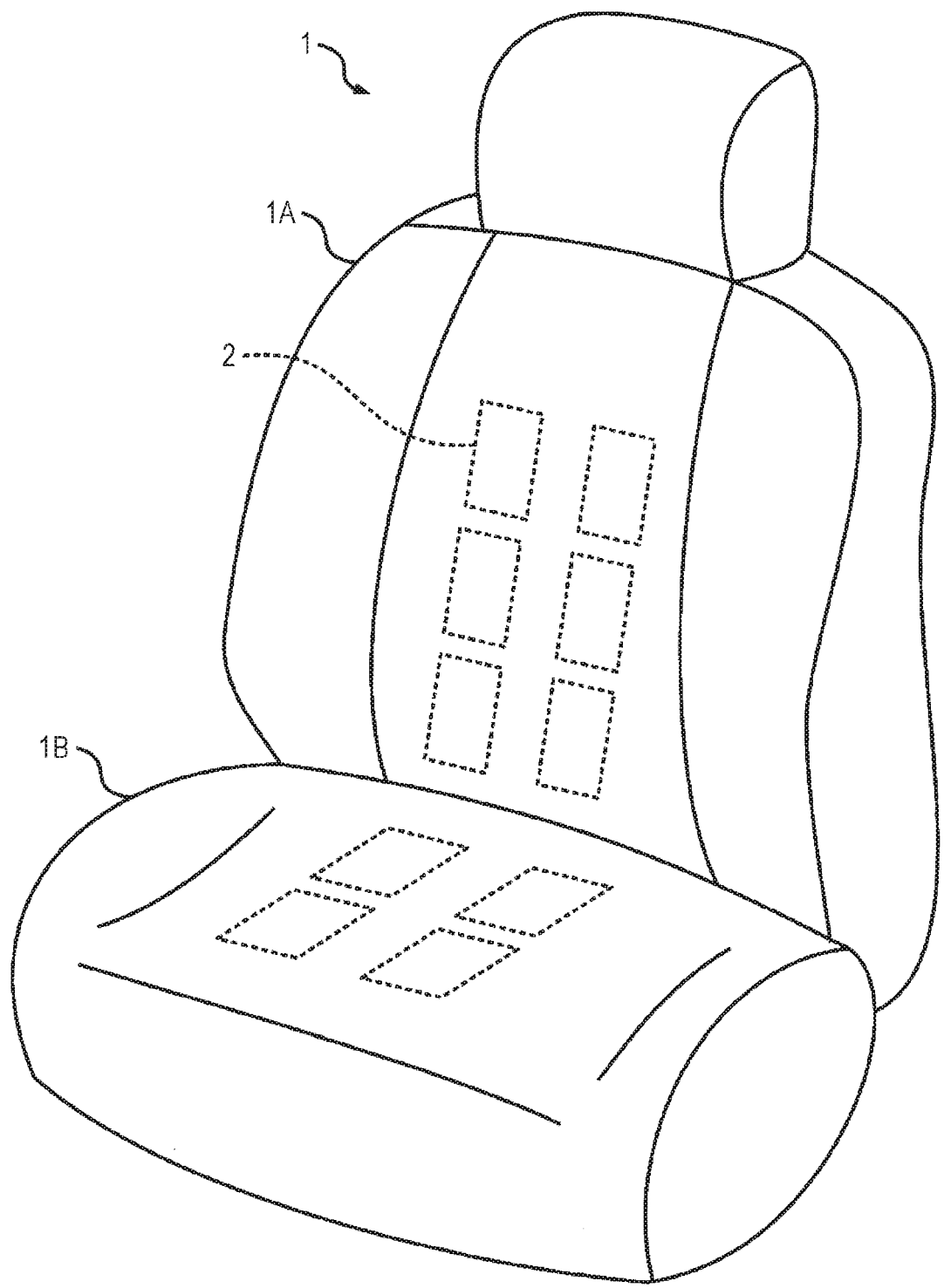
FIG. 1 illustrates an example of a vehicle seat equipped with sensor devices according to an embodiment of the present disclosure.

Embodiments of the present invention will be described below with reference to the drawings.

FIG. 1 illustrates an example of a vehicle seat 1 equipped with sensor devices 2 according to an embodiment of the present invention. In the example in FIG. 1, the vehicle seat 1 has a backrest 1A and a seat 1B. A plurality of sensor devices 2 are provided inside the surfaces of the backrest 1A and seat 1B. The vehicle seat 1 may have a function for blowing air to be used for temperature adjustment from, for example, the surface of the backrest 1A or seat 1B. In this case, since the sensor device 2 according to this embodiment has air permeability, the sensor device 2 does not hinder a flow of air. Therefore, the sensor devices 2 can be provided at appropriate positions in the backrest 1A and seat 1B without affecting the temperature adjustment function, so the sensor device 2 can detect information about a live body (such as a change in the motion of the body and an electric signal generated by the live body) with good sensitivity.

The sensor device 2 may have an electrode cover that faces the outside of the vehicle seat 1 and is made of a non-woven fabric having a color similar to the color of the outer surface of the vehicle seat 1, as will be described later. Since this electrode cover covers the electrodes (formed from a conductive fabric), it is possible to prevent the electrodes from being noticeable from the outside.

Sensor devices according to embodiments of the present invention will be described below.

First Embodiment

FIG. 2 illustrates an example of a sensor device 2A according to a first embodiment, illustrating an example of the outside shape of the sensor device 2A when viewed from directions toward the front, side, and back. The sensor device 2A illustrated in FIG. 2 has conductive fabrics 21 and 22, each of which forms an electrode, an insulative non-woven fabric 31, and a substrate 10.

An example of the conductive fabrics 21 and 22 is a fabric that is formed from chemical fibers such as polyester fibers, the surface of which is coated with a metal (conductor) such as copper or nickel. Another example is a fabric that is formed from a fabric material including a conductive material (such as carbon). Conductive fabrics 23 to 27 in embodiments described later are also formed from a material similar to the material for the conductive fabrics 21 and 22.

The non-woven fabric 31 is a sheet-like member with insulative fibers intertwined and spread like a plane. The non-woven fabric 31 is formed from, for example, synthetic fibers such as polyester fibers or polyimide fibers or inorganic fibers such as glass fibers. Non-woven fabrics 33 to 37 in embodiments described later are also formed from materials similar to the material for the non-woven fabric 31.

The two conductive fabrics 21 and 22 face each other with the non-woven fabric 31 located in between. The conductive fabric 21 is joined to the surface of the non-woven fabric 31 on the front side, and the conductive fabric 22 is joined to the surface of the non-woven fabric 31 on the back side. The joining of the conductive fabrics 21 and 22 to the non-woven fabric 31 is performed by, for example, fusion or seaming. In joining by fusion, heat or vibration is applied to a place of joining or the place is illuminated with a laser beam, in a state in which the conductive fabrics 21 and 22 and non-woven fabric 31 are overlaid on each other, for example. In joining by seaming, an insulative thread such as, for example, a synthetic fiber is used to sew the conductive fabric 21 and non-woven fabric 31 together and sew the conductive fabric 22 and non-woven fabric 31 together.

In FIG. 2, P1 indicates a place of joining between the conductive fabric 21 and the non-woven fabric 31, and P2 indicates a place of joining between the conductive fabric 22 and the non-woven fabric 31. As illustrated in FIG. 2, there is preferably a displacement in a plan view of the sensor device 2A between the joining place P1, where the conductive fabric 21 is joined to the non-woven fabric 31, and the joining place P2, where the conductive fabric 22 is joined to the non-woven fabric 31. That is, the joining place P1 and joining place P2 are not overlaid on each other.

As illustrated in FIG. 2, most of the overlaid portion between the conductive fabrics 21 and 22 is included inside the outer edges of the conductive fabric 22 in a plan view of the sensor device 2A. That is, the conductive fabric 21 as a whole is smaller than the conductive fabric 22, and most of the conductive fabric 21 is included in the area of the conductive fabric 22 in a plan view. The joining place P2 between the conductive fabric 22 and the non-woven fabric 31 partially encloses the circumference of the conductive fabric 21 in a plan view.

As illustrated in FIG. 2, the outer edges of the conductive fabric 21 and the outer edges of the conductive fabric 22 are separated from each other in a plan view of the sensor device 2A in a state in which part of at least one surface (surface on the front side or surface on the back side) of the non-woven fabric 31 interposed between the conductive fabrics 21 and 22. That is, the outer edges of the conductive fabric 21 and the outer edges of the conductive fabric 22 are preferably distant from each other in a direction along the surface of the non-woven fabric 31.

The substrate 10 includes an electronic circuit connected to the two conductive fabrics 21 and 22. This electronic circuit includes an amplifier circuit and the like. The amplifier uses one electrode (conductive fabric 21, for example) as a detection electrode and amplifies an electric signal entered due to capacitive coupling between the detection electrode and a live body. In this case, the other electrode (conductive fabric 22, for example) functions as a shield electrode controlled so as, for example, to have the same potential as the detection electrode. Alternatively, the electronic circuit of the substrate 10 may be a circuit that detects a change in capacitance (mutual capacitance) formed by the two electrodes (conductive fabrics 21 and 22). In this case, the electronic circuit detects a minute motion of the live body in response to the change in capacitance. The conductive fabrics 21 and 22 are connected to wiring patterns on the substrate 10 by, for example, soldering.

FIGS. 3A to 3C, 4A, and 4B illustrate an example of a method of manufacturing the sensor device 2A illustrated in FIG. 2.

FIG. 3A illustrates a state in which nothing is attached to the non-woven fabric 31. In this state in FIG. 3A, the conductive fabric 21 is disposed on the surface of the non-woven fabric 31 on the front side as illustrated in FIG. 3B, and the non-woven fabric 31 and conductive fabric 21 are preferably joined together by at least one of fusion and seaming as illustrated in FIG. 3C.

After that, the conductive fabric 22 is disposed on the surface of the non-woven fabric 31 on the back side as illustrated in FIG. 4A, and the non-woven fabric 31 and conductive fabric 22 are preferably joined together by at least one of fusion and seaming as illustrated in FIG. 4B. At this time, as the joining place P2 between the non-woven fabric 31 and the conductive fabric 22, a place is selected where the place does not overlay the joining place P1 between the non-woven fabric 31 and the conductive fabric 21 and where the conductive fabric 21 is not located.

As described above, with the sensor device 2A in this embodiment, electrodes are formed by the conductive fabrics 21 and 22, the conductive fabric 21 being joined to the surface of the insulative non-woven fabric 31 on the front side, the conductive fabric 22 being joined to the surface of the insulative non-woven fabric 31 on the back side. Therefore, air permeability and flexibility can be assured. The conductive fabrics 21 and 22 and the non-woven fabric 31 are joined together by at least one of fusion and seaming, making it difficult for air permeability or flexibility to be impaired. Furthermore, since the non-woven fabric 31 does not easily cause a ravel unlike a woven fabric and knitted fabric, it is possible to effectively suppress a decrease in the insulation property of the conductive fabrics 21 and 22, each of which forms an electrode. In addition, since the porosity (density of clearances) of the non-woven fabric 31 is easily adjusted when compared with woven work and knitted work, a tradeoff between air permeability and the insulation property can be appropriately set depending on the use situation or the like.

With the sensor device 2A in this embodiment, there is a displacement in a plan view of the sensor device 2A between the joining place P1, where the conductive fabric 21 is joined to the non-woven fabric 31, and the joining place P2, where the conductive fabric 22 is joined to the non-woven fabric 31. Therefore, the conductive fabrics 21 and 22 can be stably insulated from each other.

With the sensor device 2A in this embodiment, the outer edges of the conductive fabric 21 and the outer edges of the conductive fabric 22 are distant from each other in a direction along a surface (surface on the front side or surface on the back side) of the non-woven fabric 31. Therefore, the conductive fabrics 21 and 22 can be more stably insulated from each other.

Second Embodiment

FIG. 5 illustrates an example of a sensor device 2B according to a second embodiment. The sensor device 2B illustrated in FIG. 5 has conductive fabrics 23 and 24, each of which forms an electrode, insulative non-woven fabrics 33 and 34, and the substrate 10. The substrate 10 in the sensor device 2B is the same as the substrate 10 in the sensor device 2A already described. This is also true for the substrate 10 in sensor devices 2C and 2D described later. Differences from the sensor device 2A already described will be mainly described below.

The two conductive fabrics 23 and 24 face each other with the overlaid non-woven fabrics 33 and 34 located in between. The conductive fabric 23 is joined to the surface of the non-woven fabric 33 on the front side, and the conductive fabric 24 is joined to the surface of the non-woven fabric 34 on the back side. In FIG. 5, P3 indicates a place of joining between the conductive fabric 23 and the non-woven fabric 33, and P4 indicates a place of joining between the conductive fabric 24 and the non-woven fabric 34. In the example in FIG. 5, there is preferably a displacement in a plan view of the sensor device 2B between the joining place P3, where the conductive fabric 23 is joined to the non-woven fabric 33, and the joining place P4, where the conductive fabric 24 is joined to the non-woven fabric 34. That is, the joining place P3 and joining place P4 are not overlaid on each other.

The surface of the non-woven fabric 33 on the back side is overlaid on the surface of the non-woven fabric 34 on the front side. In FIG. 5, Q1 indicates a place of joining between the non-woven fabric 33 and the non-woven fabric 34. As illustrated in FIG. 5, the joining place Q1 between the non-woven fabric 33 to which the conductive fabric 23 is joined and the non-woven fabric 34 to which the conductive fabric 24 is joined is preferably positioned outside the areas of the conductive fabrics 23 and 24 in a plan view of the sensor device 2B.

Joining between the conductive fabric 23 and the non-woven fabric 33, joining between the conductive fabric 24 and the non-woven fabric 34, and joining between the non-woven fabrics 33 and 34 are performed by fusion or seaming as with the sensor device 2A already described.

As illustrated in FIG. 5, the outer edges of the conductive fabric 23 and the outer edges of the conductive fabric 24 are separated from each other in a plan view of the sensor device 2B in a state in which part of at least one surface of the non-woven fabrics 33 and 34 (surface of the non-woven fabric 33 on the front side or surface of the non-woven fabric 34 on the back side) interposed between the conductive fabrics 23 and 24. That is, the outer edges of the conductive fabric 23 and the outer edges of the conductive fabric 24 are preferably distant from each other in a direction along the surfaces of the non-woven fabrics 33 and 34.

FIGS. 6A to 6C, 7A to 7C, 8A, and 8B illustrate an example of a method of manufacturing the sensor device 2B illustrated in FIG. 5.

FIG. 6A illustrates a state in which nothing is attached to the non-woven fabric 33. In this state in FIG. 6A, the conductive fabric 23 is disposed on the surface of the non-woven fabric 33 on the front side as illustrated in FIG. 6B, and the non-woven fabric 33 and conductive fabric 23 are preferably joined together by at least one of fusion and seaming as illustrated in FIG. 6C.

FIG. 7A indicates a state in which nothing is attached to the non-woven fabric 34. In this state in FIG. 7A, the conductive fabric 24 is disposed on the surface of the non-woven fabric 34 on the back side as illustrated in FIG. 7B, and the non-woven fabric 34 and conductive fabric 24 are preferably joined together by at least one of fusion and seaming as illustrated in FIG. 7C.

After that, the surface on the back side of the non-woven fabric 33 in the state illustrated in FIG. 6C and the surface on the front side of the non-woven fabric 34 in the state illustrated in FIG. 7C are overlaid on each other as illustrated in FIG. 8A. When the non-woven fabrics 33 and 34 are placed in the overlaid state as illustrated in FIG. 8A, the two conductive fabrics 23 and 24 face each other with the non-woven fabrics 33 and 34 located in between. The non-woven fabrics 33 and 34 placed in the overlaid state are preferably joined together by at least one of fusion and seaming as illustrated in FIG. 8B. At this time, the non-woven fabrics 33 and 34 are joined together at positions outside the areas of the two conductive fabrics 23 and 24 in a plan view of the sensor device 2B.

As described above, with the sensor device 2B in this embodiment, the two opposing conductive fabrics 23 and 24 are separated from each other by the overlaid non-woven fabrics 33 and 34. Therefore, the two conductive fabrics 23 and 24 can be stably insulated from each other.

With the sensor device 2B in this embodiment, the non-woven fabric 33 to which the conductive fabric 23 on one side is joined and the non-woven fabric 34 to which the conductive fabric 24 on the other side is joined are joined together by at least one of fusion and seaming. Since the non-woven fabrics 33 and 34 are joined together as in joining between the conductive fabric 23 and the non-woven fabric 33 and joining between the conductive fabric 24 and the non-woven fabric 34, manufacturing processes can be simplified.

With the sensor device 2B in this embodiment, the non-woven fabric 33 to which the conductive fabric 23 is joined and the non-woven fabric 34 to which the conductive fabric 24 is joined are joined together outside the areas of the conductive fabrics 23 and 24 in a plan view of the sensor device 2B. Therefore, the conductive fabrics 23 and 24 can be stably insulated from each other.

With the sensor device 2B in this embodiment, there is a displacement between the joining place P3, where the conductive fabric 23 is joined to the non-woven fabric 33, and the joining place P4, where the conductive fabric 24 is joined to the non-woven fabric 34. Therefore, the conductive fabrics 23 and 24 can be stably insulated from each other.

With the sensor device 2B in this embodiment, the outer edges of the conductive fabric 23 and the outer edges of the conductive fabric 24 are distant from each other in a direction along the surface of the non-woven fabric 33 on the front side and the surface of the non-woven fabric 34 on the back side. Therefore, the conductive fabrics 23 and 24 can be stably insulated from each other.

The structure, other than the above, of the sensor device 2B according to this embodiment is similar to the structure of the sensor device 2A already described, and the sensor device 2B has an effect similar to the effect of the sensor device 2A.

Third Embodiment

FIG. 9 illustrates an example of a sensor device 2C according to a third embodiment. The sensor device 2C illustrated in FIG. 9 has conductive fabrics 25 and 26, each of which forms an electrode, insulative non-woven fabrics 35 and 36, and the substrate 10. Differences from the sensor devices 2A and 2B already described will be mainly described below.

As illustrated in FIG. 9, the two conductive fabrics 25 and 26 face each other with the non-woven fabric 35 located in between, and the two non-woven fabrics 35 and 36 face each other. The conductive fabric 25 is joined to the surface of the non-woven fabric 35 on the front side, and the conductive fabric 26 is joined to the surface of the non-woven fabric 36 on the front side. In FIG. 9, P5 indicates a place of joining between the conductive fabric 25 and the non-woven fabric 35, and P6 indicates a place of joining between the conductive fabric 26 and the non-woven fabric 36. In the example in FIG. 9, there is preferably a displacement in a plan view of the sensor device 2C between the joining place P5, where the conductive fabric 25 is joined to the non-woven fabric 35, and the joining place P6, where the conductive fabric 26 is joined to the non-woven fabric 36. That is, the joining place P5 and joining place P6 are not overlaid on each other.

The surface of the non-woven fabric 35 on the back side is overlaid on the surface of the non-woven fabric 36 on the front side, the conductive fabric 26 being joined to the surface of the non-woven fabric 36 on the front side. In FIG. 9, Q2 indicates a place of joining between the non-woven fabrics 35 and 36. As illustrated in FIG. 9, the joining place Q2 between the non-woven fabric 35 to which the conductive fabric 25 is joined and the non-woven fabric 36 to which the conductive fabric 26 is joined is preferably positioned outside the areas of the conductive fabrics 25 and 26 in a plan view of the sensor device 2C.

Joining between the conductive fabric 25 and the non-woven fabric 35, joining between the conductive fabric 26 and the non-woven fabric 36, and joining between the non-woven fabrics 35 and 36 are performed by fusion or seaming as with the sensor devices 2A and 2B already described.

As illustrated in FIG. 9, the conductive fabrics 25 and 26 as a whole are smaller than the non-woven fabric 35 in a plan view of the sensor device 2C, and most of the conductive fabrics 25 and 26 are included in the area of the non-woven fabric 35 in a plan view. The outer edges of the conductive fabric 25 and the outer edges of the conductive fabric 26 are separated from each other in a state in which part of at least one surface (surface on the front side or surface on the back side) of the non-woven fabric 35 interposed between the conductive fabrics 25 and 26, in a plan view of the sensor device 2C. That is, the outer edges of the conductive fabric 25 and the outer edges of the conductive fabric 26 are preferably distant from each other in a direction along the surface of the non-woven fabric 35.

FIGS. 10A to 10C, 11A to 11C, 12A, and 12B illustrate an example of a method of manufacturing the sensor device 2C illustrated in FIG. 9.

FIG. 10A illustrates a state in which nothing is attached to the non-woven fabric 35. In this state in FIG. 10A, the conductive fabric 25 is disposed on the surface of the non-woven fabric 35 on the front side as illustrated in FIG. 10B, and the non-woven fabric 35 and conductive fabric 25 are joined together by at least one of fusion and seaming as illustrated in FIG. 10C.

FIG. 11A illustrates a state in which nothing is attached to the non-woven fabric 36. In this state in FIG. 11A, the conductive fabric 26 is disposed on the surface of the non-woven fabric 36 on the front side as illustrated in FIG. 11B, and the non-woven fabric 36 and conductive fabric 26 are joined together by at least one of fusion and seaming as illustrated in FIG. 11C.

After that, the surface on the back side of the non-woven fabric 35 in the state illustrated in FIG. 10C, and the surface on the front side of the non-woven fabric 36 in the state illustrated in FIG. 11C are overlaid on each other as illustrated in FIG. 12A. When the non-woven fabrics 35 and 36 are placed in the overlaid state as illustrated in FIG. 12A, the two conductive fabrics 25 and 26 face each other with the non-woven fabric 35 located in between. The conductive fabric 26 is in a state in which both surfaces of the conductive fabric 26 are covered by the two non-woven fabrics 35 and 36. The non-woven fabrics 35 and 36 placed in the overlaid state are joined together by at least one of fusion and seaming as illustrated in FIG. 12B. At this time, the non-woven fabrics 35 and 36 are joined together at positions outside the areas of the two conductive fabrics 25 and 26 in a plan view of the sensor device 2C.

As described above, with the sensor device 2C in this embodiment, the two opposing conductive fabrics 25 and 26 are separated from each other by the non-woven fabric 35. Therefore, the two conductive fabrics 25 and 26 can be stably insulated from each other. Since the conductive fabric 26 is interposed between the two non-woven fabrics 35 and 36, the insulation property for the conductive fabric 26 can be enhanced.

The structure, other than the above, of the sensor device 2C according to this embodiment is similar to the structures of the sensor devices 2A and 2B already described, and the sensor device 2C has an effect similar to the effect of the sensor devices 2A and 2B.

Fourth Embodiment

FIG. 13A illustrates an example of a sensor device 2D according to a fourth embodiment. FIG. 13B illustrates the sensor device 2D illustrated in FIG. 13A, in a state in which an electrode cover 41 is not illustrated. In the sensor device 2D illustrated in FIG. 13A, the surface, of the conductive fabric 25, exposed to the outside in the already-described sensor device 2C illustrated in FIG. 9 (the surface is opposite to the surface in contact with the non-woven fabric 35) is preferably covered with the insulative electrode cover 41. The other structure is almost the same as in the sensor device 2C illustrated in FIG. 9. In the sensor device 2D, however, the non-woven fabric 36 in the sensor device 2C is replaced with a non-woven fabric 36A, which is slightly larger in size than the non-woven fabric 36.

The electrode cover 41 is preferably formed from an insulative non-woven fabric and is preferably joined to the non-woven fabric 36A by fusion or seaming. Q3 in FIG. 13A indicates a place where the electrode cover 41 and non-woven fabric 36A are joined together. As illustrated in FIG. 13A, the joining place Q3 between the electrode cover 41 and the non-woven fabric 36A is positioned outside the areas of the conductive fabrics 25 and 26.

Since, in the sensor device 2D according to this embodiment, the surface, exposed to the outside, of the conductive fabric 25 is covered with the electrode cover 41 formed from an insulative non-woven fabric as described above, the insulation property for the conductive fabric 25 can be enhanced. Since the non-woven fabric 36A and electrode cover 41 are joined together as in joining between the conductive fabric 25 and the non-woven fabric 36 and joining between the conductive fabric 26 and the non-woven fabric 36A, manufacturing processes can be simplified.

When the sensor device 2D is disposed inside the vehicle seat 1 (FIG. 1), the sensor device 2D may be disposed so that the electrode cover 41 faces the outside of the vehicle seat 1 and the electrode cover 41 may have the same color as the outer surface of the vehicle seat 1. Thus, since the conductive fabric 25 is covered with the electrode cover 41 that faces the outside of the vehicle seat 1 and that has the same color as the outer surface of the vehicle seat 1, it is possible to make the conductive fabric 25 less likely to be noticeable from the outside and to make the electrode cover 41 itself less likely to be noticeable.

So far, sensor devices according to embodiments of the present invention have been described. However, the present invention is not limited only to the embodiments described above but various variations and modifications are possible without departing from the scope of the present invention.

FIG. 14 illustrates a variation of a sensor device according to an embodiment of the present invention.

A sensor device 2E illustrated in FIG. 14 has an insulative non-woven fabric 37 and a plurality of conductive fabrics 27A to 27F joined to one surface of the non-woven fabric 37 by fusion or seaming. On the surface of the non-woven fabric 37, to which the conductive fabrics 27A to 27F are joined, wiring patterns 51A to 51F electrically continuous to the conductive fabrics 27A to 27F are preferably formed in advance. The wiring patterns 51A to 51F are formed on the surface of the non-woven fabric 37 by, for example, a film forming method such as sputtering. When the conductive fabrics 27A to 27F and the wiring patterns 51A to 51F formed on the surface of the non-woven fabric 37 in advance electrically are made continuous to each other in this way, it is unnecessary to connect these conductive fabrics to other wires such as electronic circuits by using connectors. Therefore, assembling processes can be simplified and the number of parts can be reduced. Since positions at which to dispose the conductive fabrics 27A to 27F on the surface of the non-woven fabric 37 are clear, work to position the conductive fabrics 27A to 27F is easy, making it possible to improve the efficiency of manufacturing.

Although, in FIG. 1, an example in which sensor devices 2 are disposed inside the vehicle seat 1 is illustrated, the present invention is not limited to this example. In another example of the present invention, sensor devices 2 may be disposed, for example, inside the lining (interior cover) of a vehicle. In this case, when an electrode cover that faces the outer surface side of the lining and has the same color as the outer surface of the lining is used, it is possible to make the conductive fabric covered with the electrode cover and the electrode cover itself less likely to be noticeable from the outside.

In the examples in the first to fourth embodiments described above, one conductive fabric is attached to each of the surface of a non-woven fabric on the front side and the surface thereof on the back side. However, a plurality of conductive fabrics may be attached to each surface of the non-woven fabric. The same number of conductive fabrics may be attached to the surface of a non-woven fabric on the front side and the surface thereof on the back side, or a different number of conductive fabrics may be attached to these surfaces.

The shapes and sizes of the conductive fabrics and non-woven fabrics and their positional relationships taken as examples in the first to fourth embodiments described above are merely examples, and may be appropriately changed.

This application claims priority based on Japanese Patent Application No. 2017-241148 filed on Dec. 15, 2017, and the entire contents of the Japanese Patent application are incorporated in this application by reference.

What is claimed is:

1. A sensor device comprising:
    an insulative non-woven fabric;
    a first conductive fabric forming an electrode, the first conductive fabric being provided on a first surface of the insulative non-woven fabric, the first conductive fabric being joined to the first surface of the insulative non-woven fabric at a first joining portion by at least one of fusion and seaming; and
    a second conductive fabric facing the first conductive fabric with the insulative non-woven fabric interposed therebetween, the second conductive fabric being joined to a second surface of the insulative non-woven fabric at a second joining portion by at least one of fusion and seaming,
    wherein the first joining portion is disposed along substantially an entire outer periphery of the first conductive fabric, and the second joining portion is disposed along substantially an entire outer periphery of the second conductive fabric, such that the first joining portion and the second joining portion being displaced from each other in a plan view of the sensor device, and that the second joining portion substantially surrounds outer edges of the first conductive fabric in the plan view,
    wherein the insulative non-woven fabric includes a first extension and a second extension extending from a side thereof in the plan view,
    and wherein the first conductive fabric includes a first extending portion joined to the first extension, and the second conductive fabric includes a second extending portion joined to the second extension.

2. The sensor device according to claim 1, wherein an outer edge of the first conductive fabric and an outer edge of the second conductive fabric are distant from each other in a direction along the first surface of the insulative non-woven fabric in the plan view.

3. The sensor device according to claim 1,
    wherein the second joining portion surrounds the outer edges of the first conductive fabric except the first extending portion in the plan view, such that the second joining portion does not intersect a joining portion of the first extending portion to the insulative non-woven fabric in the plan view.

4. The sensor device according to claim 1,
wherein the first extending portion of the first conductive fabric extending beyond an end of the first extension of the insulative non-woven fabric in the plan view, and the second extending portion of the second conductive fabric extending beyond an end of the second extension of the insulative non-woven fabric in the plan view.

5. The sensor device according to claim 1, further comprising:
a wiring pattern formed on the first surface of the insulative non-woven fabric, the wiring pattern being electrically continuous to the first conductive fabric joined to the first surface of the insulative non-woven fabric.

6. A method of manufacturing a sensor device of claim 1, the method comprising:
joining the first conductive fabric to the first surface of the insulative non-woven fabric at the first joining portion by at least one of fusion and seaming; and
after joining the first conductive fabric, joining the second conductive fabric to the second surface of the insulative non-woven fabric opposite to the first surface at the second joining portion, by at least one of fusion and seaming, wherein the first joining portion and the second joining portion are displaced from each other in a plan view of the sensor device.

7. A vehicle seat comprising the sensor device according to claim 1 disposed inside the vehicle seat.

8. A sensor device comprising:
a first insulative non-woven fabric;
a first conductive fabric forming an electrode, the first conductive fabric being provided on and joined to a first surface of the first insulative non-woven fabric at a first joining portion by at least one of fusion and seaming;
a second insulative non-woven fabric overlaid on a second surface of the first insulative non-woven fabric; and
a second conductive fabric facing the first conductive fabric with the first insulative non-woven fabric and the second insulative non-woven fabric interposed therebetween, the second conductive fabric being joined to a first surface of the second insulative non-woven fabric adjacent to the second conductive fabric at a second joining portion by at least one of fusion and seaming, the second joining portion substantially surrounding the outer edges of the first conductive fabric in a plan view of the sensor device,
wherein the first insulative non-woven fabric and the second insulative non-woven fabric are joined together at a third joining portion by at least one of fusion and seaming, the third joining portion being positioned outside of an area in which the first conductive fabric and the second conductive fabric are disposed, such that the third joining portion substantially surrounds outer edges of the first and second conductive fabrics in the plan view,
wherein the first insulative non-woven fabric includes a first extension, and the second insulative non-woven fabric includes a second extension which does not overlap the first extension in the plan view,
and wherein the first conductive fabric includes a first extending portion joined to the first extension, and the second conductive fabric includes a second extending portion joined to the second extension.

9. The sensor device according to claim 8,
wherein the first joining portion is disposed along substantially an entire outer periphery of the first conductive fabric,
and wherein the second joining portion is disposed along substantially an entire outer periphery of the second conductive fabric.

10. The sensor device according to claim 8,
wherein the third joining portion surrounds the outer edges of the first and second conductive fabrics except the first and second extending portions in the plan view, such that the third joining portion does not intersect joining portions of the first and second extending portions to the first and second insulative non-woven fabrics, respectively, in the plan view.

11. The sensor device according to claim 8,
wherein the first extending portion of the first conductive fabric extending beyond an end of the first extension of the first insulative non-woven fabric in the plan view, and the second extending portion of the second conductive fabric extending beyond an end of the second extension of the second insulative non-woven fabric in the plan view.

12. A method of manufacturing a sensor device of claim 8, the method comprising:
joining the first conductive fabric to the first surface of the first insulative non-woven fabric by at least one of fusion and seaming;
joining the second conductive fabric to the first surface of the second insulative non-woven fabric by at least one of fusion and seaming; and
joining the first insulative non-woven fabric having the first conductive fabric joined thereto and the second insulative non-woven fabric having the second conductive fabric joined thereto together by at least one of fusion and seaming such that the second surface of the first insulative non-woven fabric and a second surface of the second insulative non-woven fabric face each other, whereby the first conductive fabric and the second conductive fabric face each other with the first insulative non-woven fabric and the second insulative non-woven fabric interposed therebetween between,
wherein the first insulative non-woven fabric and the second insulative non-woven fabric are joined together at a position outside of an area in which the first conductive fabric and the second conductive fabric are disposed in a plan view of the sensor device.

13. A sensor device comprising:
a first insulative non-woven fabric;
a first conductive fabric forming an electrode, the first conductive fabric being provided on and joined to a first surface of the first insulative non-woven fabric at a first joining portion;
a second conductive fabric facing the first conductive fabric with the first insulative non-woven fabric interposed therebetween; and
a second insulative non-woven fabric facing the first insulative non-woven fabric with the second conductive fabric located therebetween, wherein the second conductive fabric is joined to a first surface of the second insulative non-woven fabric facing the first insulative non-woven fabric at a second joining portion by at least one of fusion and seaming, the second joining portion substantially surrounding the outer edges of the first conductive fabric in a plan view of the sensor device,
wherein the first insulative non-woven fabric and the second insulative non-woven fabric are joined together at a third joining portion by at least one of fusion and seaming, the third joining portion being positioned outside of an area in which the first conductive fabric and the second conductive fabric are disposed in the plan view, such that the third joining portion substantially surrounds outer edges of the first and second conductive fabrics in the plan view, wherein the first insulative non-woven fabric includes a first extension, and the second insulative non-woven fabric includes a second extension which does not overlap the first extension in the plan view, and wherein the first conductive fabric includes a first extending portion joined to the first extension, and the second conductive fabric includes a second extending portion joined to the second extension.

14. The sensor device according to claim 13, wherein the first joining portion is disposed along substantially an entire outer periphery of the first conductive fabric, and wherein the second joining portion is disposed along substantially an entire outer periphery of the second conductive fabric.

15. The sensor device according to claim 13, wherein the third joining portion surrounds the outer edges of the first and second conductive fabrics except the first and second extending portions in the plan view, such that the third joining portion does not intersect joining portions of the first and second extending portions to the first and second insulative non-woven fabrics, respectively, in the plan view.

16. The sensor device according to claim 13, wherein the first extending portion of the first conductive fabric extending beyond an end of the first extension of the first insulative non-woven fabric in the plan view, and the second extending portion of the second conductive fabric extending beyond an end of the second extension of the second insulative non-woven fabric in the plan view.

17. The sensor device according to claim 13, further comprising:

an electrode cover formed of another insulative non-woven fabric, the electrode cover covering a surface of the first conductive fabric opposite to a surface thereof in contact with the first insulative non-woven fabric, wherein the electrode cover and the second insulative non-woven fabric to which the second conductive fabric is joined are joined together by at least one of fusion and seaming.

18. The sensor device according to claim 17, wherein:

the sensor device is disposed inside a vehicle seat or a lining of a vehicle so that the electrode cover faces an outside of the vehicle seat or an outside of the lining, and the electrode cover has the same color as an outer surface of the vehicle seat or an outer surface of the lining.

19. A method of manufacturing a sensor device of claim 13, the method comprising:

joining the first conductive fabric to the first surface of the first insulative non-woven fabric by at least one of fusion and seaming;

joining the second conductive fabric to the first surface of the second insulative non-woven fabric by at least one of fusion and seaming; and joining the first insulative non-woven fabric having the first conductive fabric joined thereto and the second insulative non-woven fabric having the second conductive fabric joined thereto together by at least one of fusion and seaming such that a second surface of the first insulative non-woven fabric and the first surface of the second insulative non-woven fabric face each other, whereby the first conductive fabric and the second conductive fabric face each other with the first insulative non-woven fabric interposed therebetween, wherein the first insulative non-woven fabric and the second insulative non-woven fabric are joined together at a position outside of an area in which the first conductive fabric and the second conductive fabric are disposed in a plan view of the sensor device.

* * * * *